United States Patent
Oostman, Jr. et al.

(10) Patent No.: US 9,084,465 B2
(45) Date of Patent: Jul. 21, 2015

(54) BIOLOGICAL UNIT REMOVAL TOOLS AND METHODS

(71) Applicant: Restoration Robotics, Inc., San Jose, CA (US)

(72) Inventors: Clifford A. Oostman, Jr., Hansville, WA (US); Miguel G. Canales, Los Altos, CA (US)

(73) Assignee: Restoration Robotics, Inc., San Jose, CA (US)

( * ) Notice: Subject to any disclaimer, the term of this patent is extended or adjusted under 35 U.S.C. 154(b) by 0 days.

(21) Appl. No.: 14/513,454

(22) Filed: Oct. 14, 2014

(65) Prior Publication Data
US 2015/0032129 A1    Jan. 29, 2015

Related U.S. Application Data

(63) Continuation of application No. 13/409,834, filed on Mar. 1, 2012, now Pat. No. 8,882,784, which is a continuation of application No. 12/050,917, filed on Mar. 18, 2008, now Pat. No. 8,133,237.

(60) Provisional application No. 60/895,530, filed on Mar. 19, 2007.

(51) Int. Cl.
*A61B 17/50* (2006.01)
*A45D 26/00* (2006.01)
(Continued)

(52) U.S. Cl.
CPC ............ *A45D 26/00* (2013.01); *A61B 10/0266* (2013.01); *A61B 17/322* (2013.01);
(Continued)

(58) Field of Classification Search
CPC ............... A45D 26/00; A61B 10/0266; A61B 10/0275; A61B 17/32053; A61B 17/32093; A61B 17/322; A61B 2010/0208; A61B 2017/00752; A61B 2017/00969; A61B 2017/320064; A61B 2217/005; A61B 2217/007; A61F 2/10

USPC .............. 30/113.1–113.3, 358; 600/564, 566, 600/567; 606/131, 133, 167, 184, 185
See application file for complete search history.

(56) References Cited

U.S. PATENT DOCUMENTS

| 3,561,429 A | 2/1971 | Jewett et al. |
| 3,605,721 A | 9/1971 | Hallac |

(Continued)

FOREIGN PATENT DOCUMENTS

| EP | 0966920 | 12/1999 |
| EP | 1293167 | 3/2003 |

(Continued)

OTHER PUBLICATIONS

Examiner's First Report in connection with commonly assigned, Australian Patent Application No. 2008229393, Applicant: Restoration Robotics Inc., dated Jun. 7, 2010, 3 pages.

(Continued)

*Primary Examiner* — Ashley Fishback
(74) *Attorney, Agent, or Firm* — Lena I Vinitskaya; Sharon Upham

(57) ABSTRACT

Tools and methods are provided for removing biological units from a body surface utilizing a removal tool. The tools may incorporate retention members and mechanisms configured to impede movement of the biological unit in the direction of a distal end of the tool and to improve retention of the biological unit in the tool. Some of the retention members are stationary and some are movable within the lumen of the biological unit removal tools. The distal tips of the tools are desirably configured to reduce the chance of transection of a biological unit, such as by including both cutting segments and blunt relief segments. A number of dual concentric tube embodiments permit a division of removal functions. Distal fluid or gas delivery may be used to help separating biological units from surrounding tissue.

20 Claims, 26 Drawing Sheets

(51) Int. Cl.
*A61B 10/02* (2006.01)
*A61B 17/3205* (2006.01)
*A61B 17/322* (2006.01)
*A61F 2/10* (2006.01)
*A61B 17/3209* (2006.01)
*A61B 17/00* (2006.01)
*A61B 17/32* (2006.01)

(52) U.S. Cl.
CPC ............ *A61B17/32053* (2013.01); *A61F 2/10* (2013.01); *A61B 10/0275* (2013.01); *A61B 17/32093* (2013.01); *A61B 2010/0208* (2013.01); *A61B 2017/00752* (2013.01); *A61B 2017/00969* (2013.01); *A61B 2017/320064* (2013.01); *A61B 2217/005* (2013.01); *A61B 2217/007* (2013.01)

(56) References Cited

U.S. PATENT DOCUMENTS

| | | |
|---|---|---|
| 3,998,230 A | 12/1976 | Miller |
| 4,160,453 A | 7/1979 | Miller |
| 4,393,872 A | 7/1983 | Reznik et al. |
| 4,479,291 A | 10/1984 | Yamada |
| 4,640,296 A | 2/1987 | Schnepp-Pesch et al. |
| 4,708,147 A | 11/1987 | Haaga |
| 4,716,901 A | 1/1988 | Jackson et al. |
| 4,785,826 A | 11/1988 | Ward |
| 5,036,860 A | 8/1991 | Leigh et al. |
| 5,183,053 A | 2/1993 | Yeh et al. |
| 5,341,816 A | 8/1994 | Allen |
| 5,423,330 A | 6/1995 | Lee |
| 5,439,475 A | 8/1995 | Bennett |
| 5,480,388 A | 1/1996 | Zadini et al. |
| 5,562,613 A | 10/1996 | Kaldany |
| 5,573,008 A | 11/1996 | Robinson et al. |
| 5,584,841 A | 12/1996 | Rassman |
| 5,693,064 A | 12/1997 | Arnold |
| 5,782,851 A | 7/1998 | Rassman |
| 5,782,853 A | 7/1998 | Zeevi et al. |
| 5,788,651 A | 8/1998 | Weilandt |
| 5,792,163 A | 8/1998 | Hitzig |
| 5,794,626 A | 8/1998 | Kieturakis |
| 5,817,120 A | 10/1998 | Rassman |
| 5,827,199 A | 10/1998 | Alexander |
| 5,827,297 A | 10/1998 | Boudjema |
| 5,885,226 A | 3/1999 | Rubinstein et al. |
| 5,893,853 A | 4/1999 | Arnold |
| 5,895,403 A | 4/1999 | Collinsworth |
| 5,910,121 A | 6/1999 | Paolo et al. |
| 5,961,529 A | 10/1999 | Arnold |
| 6,015,391 A | 1/2000 | Rishton et al. |
| 6,059,807 A | 5/2000 | Boudjema |
| 6,080,175 A | 6/2000 | Hogendijk |
| 6,086,543 A | 7/2000 | Anderson et al. |
| 6,110,127 A | 8/2000 | Suzuki |
| 6,110,189 A | 8/2000 | Markman |
| 6,120,521 A | 9/2000 | Casparian |
| 6,142,955 A | 11/2000 | Farascioni et al. |
| 6,273,861 B1 | 8/2001 | Bates et al. |
| 6,306,142 B1 | 10/2001 | Johanson et al. |
| 6,315,737 B1 | 11/2001 | Skinner |
| 6,395,002 B1 | 5/2002 | Ellman et al. |
| 6,416,484 B1 | 7/2002 | Miller et al. |
| 6,461,369 B1 | 10/2002 | Kim |
| 6,471,709 B1 | 10/2002 | Fawzi et al. |
| 6,488,636 B2 | 12/2002 | Bryan et al. |
| 6,527,765 B2 | 3/2003 | Kelman et al. |
| 6,554,779 B2 | 4/2003 | Viola et al. |
| 6,572,625 B1 | 6/2003 | Rassman |
| 6,585,746 B2 | 7/2003 | Gildenberg |
| 6,875,220 B2 | 4/2005 | Du et al. |
| 6,918,880 B2 | 7/2005 | Brookner et al. |
| 6,926,676 B2 | 8/2005 | Turturro et al. |
| 6,939,318 B2 | 9/2005 | Stenzel |
| 7,172,604 B2 | 2/2007 | Cole |
| 7,201,722 B2 | 4/2007 | Krueger |
| 7,261,721 B2 | 8/2007 | Feller |
| 7,278,972 B2 | 10/2007 | Lamoureux et al. |
| 7,762,959 B2 | 7/2010 | Bilsbury |
| 7,775,989 B2 | 8/2010 | Nakao et al. |
| 2001/0034534 A1 | 10/2001 | Transue |
| 2002/0103500 A1 | 8/2002 | Gildenberg |
| 2002/0151821 A1 | 10/2002 | Castellacci |
| 2003/0097079 A1 | 5/2003 | Garcia |
| 2003/0097144 A1 | 5/2003 | Lee |
| 2004/0092924 A1 | 5/2004 | Vasa |
| 2004/0116942 A1 | 6/2004 | Feller |
| 2004/0220589 A1 | 11/2004 | Feller |
| 2005/0043718 A1 | 2/2005 | Madhani et al. |
| 2005/0085838 A1 | 4/2005 | Thompson et al. |
| 2005/0090809 A1 | 4/2005 | Cooper et al. |
| 2005/0096687 A1 | 5/2005 | Rassman et al. |
| 2005/0131313 A1 | 6/2005 | Mikulka et al. |
| 2005/0187573 A1 | 8/2005 | Rassman et al. |
| 2005/0245952 A1 | 11/2005 | Feller |
| 2005/0267506 A1 | 12/2005 | Harris |
| 2006/0161179 A1 | 7/2006 | Kachenmeister |
| 2006/0173476 A1 | 8/2006 | Bradica et al. |
| 2006/0178678 A1 | 8/2006 | Cole |
| 2007/0078466 A1 | 4/2007 | Bodduluri et al. |
| 2007/0078473 A1 | 4/2007 | Bodduluri et al. |
| 2007/0106307 A1 | 5/2007 | Bodduluri et al. |
| 2007/0123800 A1 | 5/2007 | Nishtala et al. |
| 2007/0142743 A1 | 6/2007 | Provencher et al. |
| 2007/0149985 A1 | 6/2007 | Cole |
| 2007/0156164 A1 | 7/2007 | Cole et al. |
| 2007/0213634 A1 | 9/2007 | Teague |
| 2007/0213741 A1 | 9/2007 | Cole |
| 2008/0033455 A1 | 2/2008 | Rassman et al. |
| 2008/0045858 A1 | 2/2008 | Tessitore et al. |
| 2008/0154150 A1 | 6/2008 | Goldenberg |
| 2008/0154296 A1 | 6/2008 | Taylor et al. |
| 2008/0177287 A1 | 7/2008 | Rassman et al. |
| 2008/0234602 A1 | 9/2008 | Oostman et al. |
| 2008/0234698 A1 | 9/2008 | Oostman et al. |
| 2009/0227895 A1 | 9/2009 | Goldenberg |
| 2009/0240261 A1 | 9/2009 | Drews et al. |
| 2010/0082042 A1 | 4/2010 | Drews |

FOREIGN PATENT DOCUMENTS

| | | |
|---|---|---|
| GB | 2006017 | 5/1979 |
| WO | WO 97/06749 | 2/1997 |
| WO | WO 02/07602 | 1/2002 |
| WO | WO 2005/109799 | 11/2005 |
| WO | WO 2006/081556 | 8/2006 |
| WO | WO 2007/021904 | 2/2007 |
| WO | WO 2008/027829 | 3/2008 |
| WO | WO 2009/017445 | 2/2009 |

OTHER PUBLICATIONS

Examiner's Second Report, mailed Jul. 7, 2011, in connection with commonly, assigned Australian Patent Application No. 2008229393, 3 pages.
Final Office Action mailed Apr. 26, 2011, in relation to commonly assigned U.S. Appl. No. 12/050,913, 24 pages.
Non-Final Office Action dated Oct. 25, 2011, in relation to commonly assinged, U.S. Appl. No. 12/050,917, (13 pages).
Non-Final Office Action mailed Mar. 4, 2011, in relation to commonly assigned, U.S. Appl. No. 12/403,605, 8 pages.
Non-Final Office Action mailed Oct. 27, 2010, in relation to commonly assigned, U.S. Appl. No. 12/050,913, 21 pages.
Non-Final Office Action mailed Sep. 15, 2010, in relation to commonly assigned, U.S. Appl. No. 12/050,907, 15 pages.
Office Action mailed Apr. 27, 2011, in relation to commonly assigned, U.S. Appl. No. 12/050,907, 20 pages.
PCT International Search Report and Written Opinion in PCT/US2008/003623, Applicant Restoration Robotics, Inc. Forms PCT/ISA/210 and 237, dated Nov. 12, 2008, (14 pages).

(56) References Cited

OTHER PUBLICATIONS

PCT Int'l Search Report and Written Opinion in connection with commonly, assigned PCT/US2009/056775, Applicant: Restoration Robotics, Inc. Forms PCT/ISA220, 210 and 237, dated Jan. 12, 2010, 14 pages.

PCT Int'l Search Report and Written Opinion in PCT/US2009/037132, Forms PCT/ISA/220, PCT/ISA/210 and PCT/ISA/237. Application Restoration Robotics, Inc., dated May 27, 2009, 17 pages.

PCT Notification concerning Transmittal of International Preliminary, Report on Patentability in connection with commonly assigned International Application PCT/US2009/056775, Applicant Restoration Robotics, Inc., Forms PCT/IB/326, PCT/IB/373, and PCT/ISA/237, dated Apr. 14, 2011., 8 pages.

PCT Notification Concerning Transmittal of International Preliminary Report, on Patentability. International Application No. PCT/US2008/003623. Form PCT/IB/.326 & 373, and PCT/ISA/237. Mailed Oct. 1, 2009, (10 pages).

Response filed Jul. 26, 2011 to Final Office Action dated Apr. 26, 2011, in relation to commonly assigned U.S. Appl. No. 12/050,913, 12 pages.

Bernstein, et al., "New Instrumentation for Three-Step Follicular Unit Extraction", vol. 16, No. 1, Jan./Feb. 2006.

Harris, "New Methodology and Instrumentation for Follicular Unit Extraction: Lower Follicle Transection Rates and Expanded Patient Candidacy", Dermatol Surg 32, Jan. 2006.

Inaba, et al., "Androgenetic Alopecia, Modern Concepts of Pathogenesis and Treatment, 29. Operative Treatment for Androgenetic Alopecia.", 1996, pp. 238-244, 309 (9 pages).

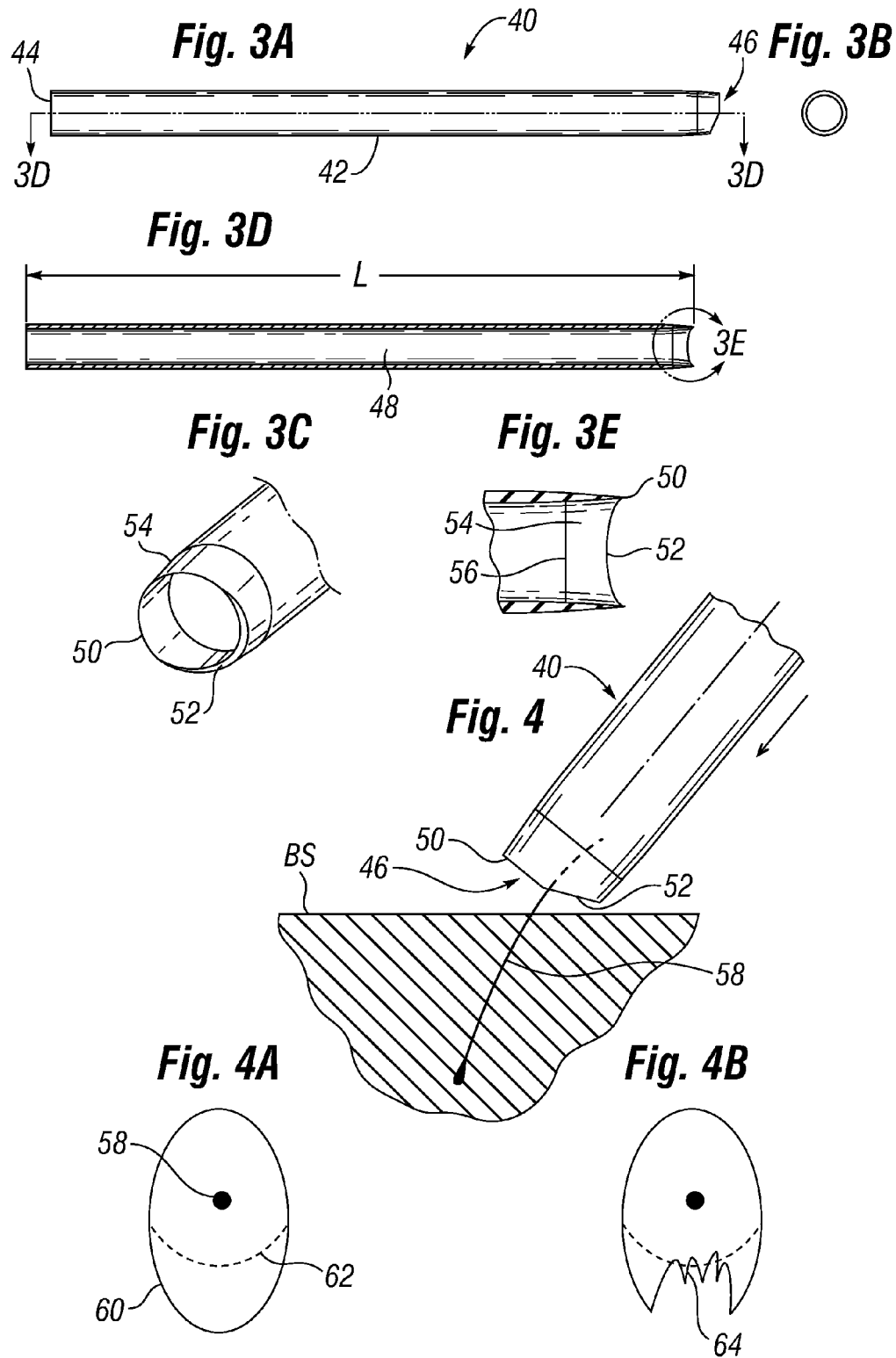

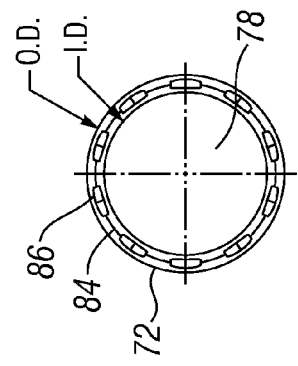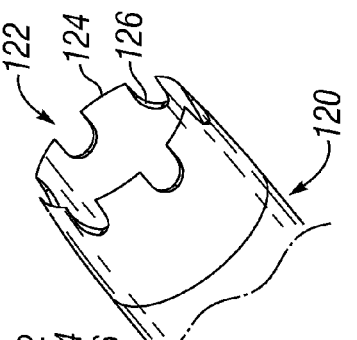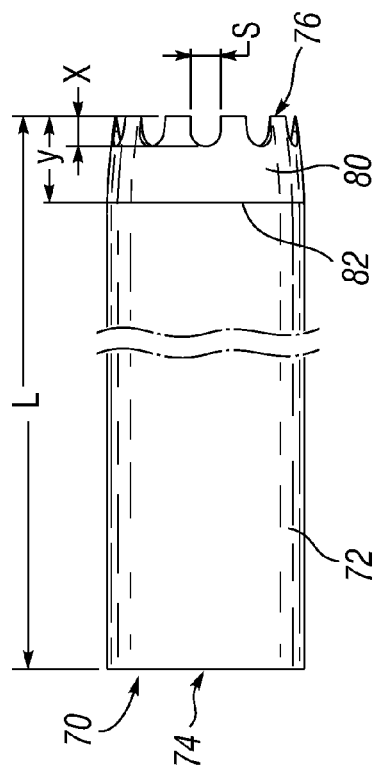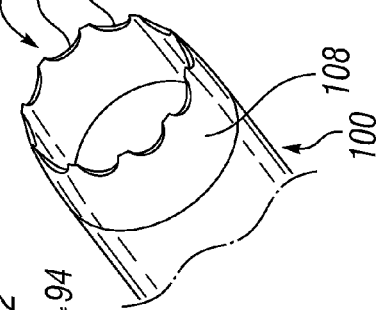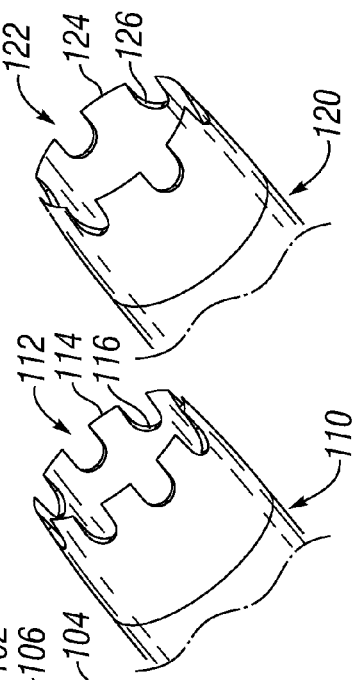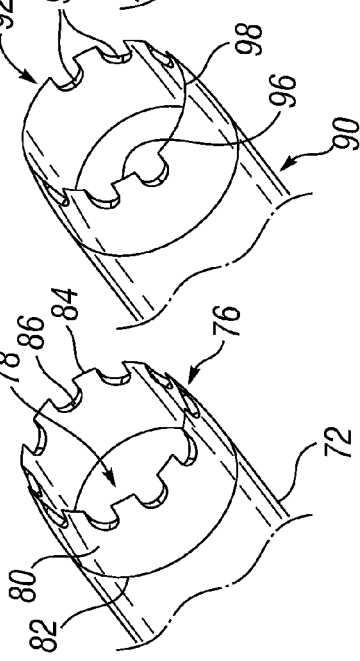

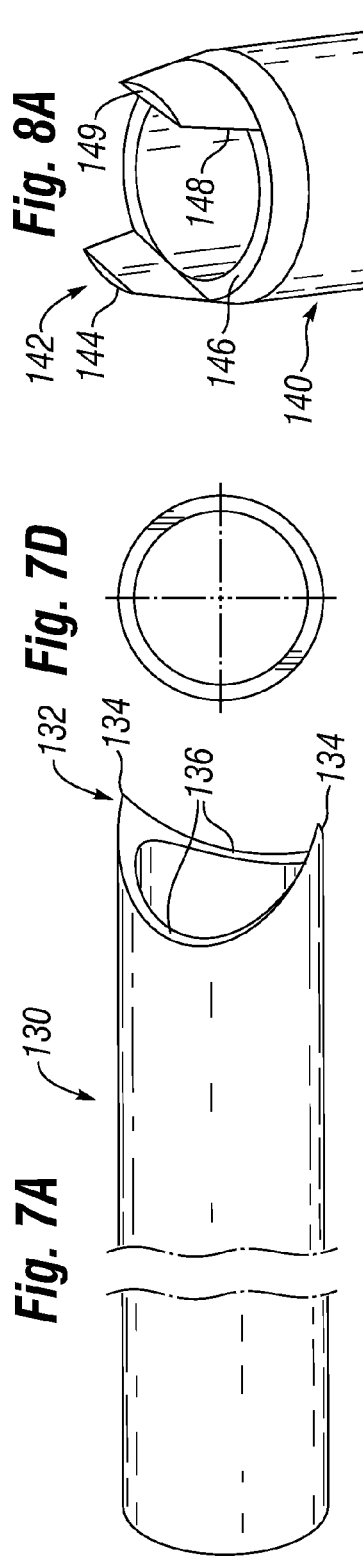
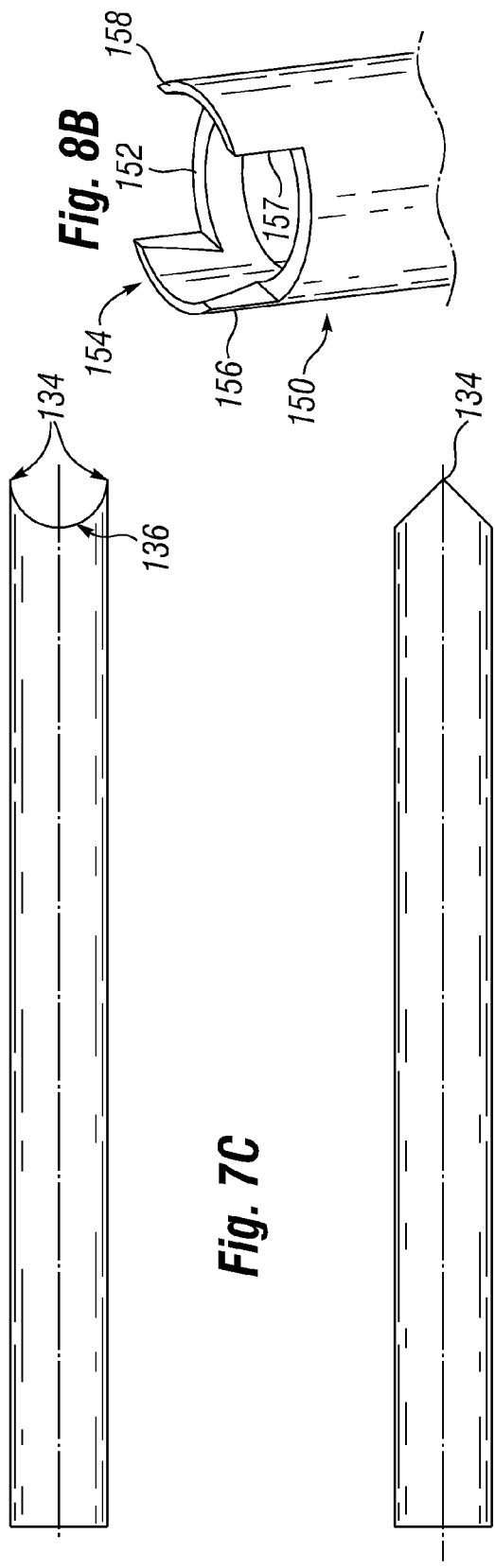

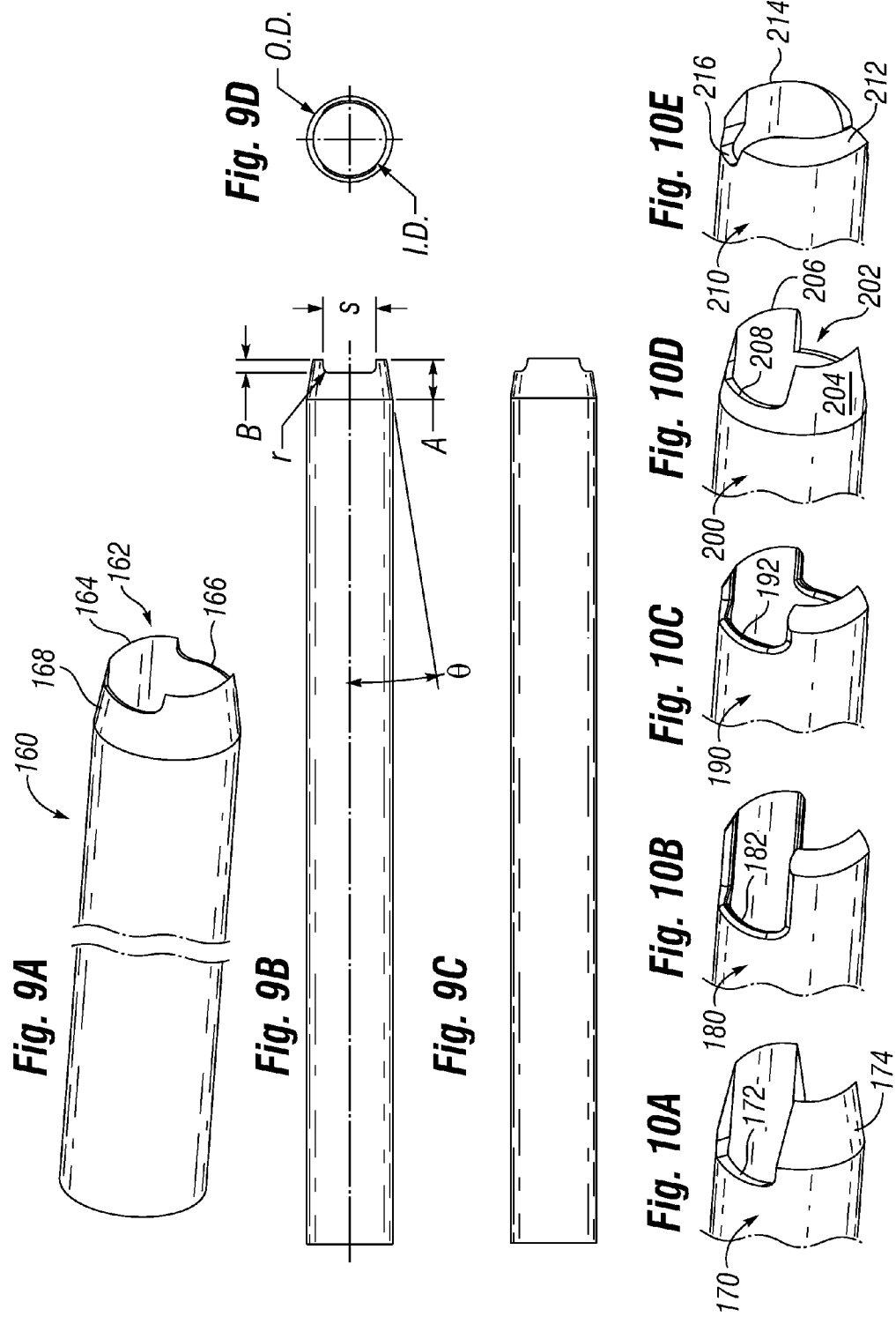

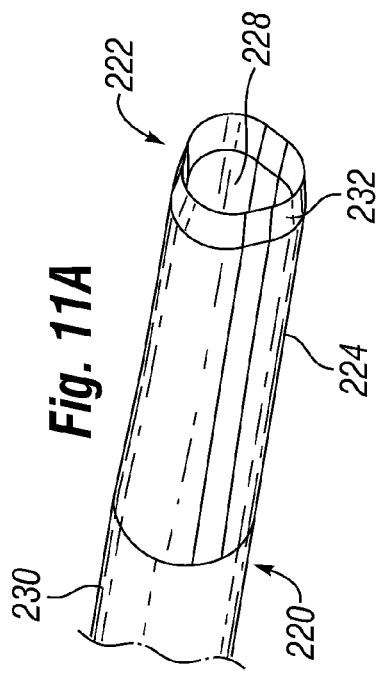
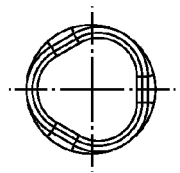
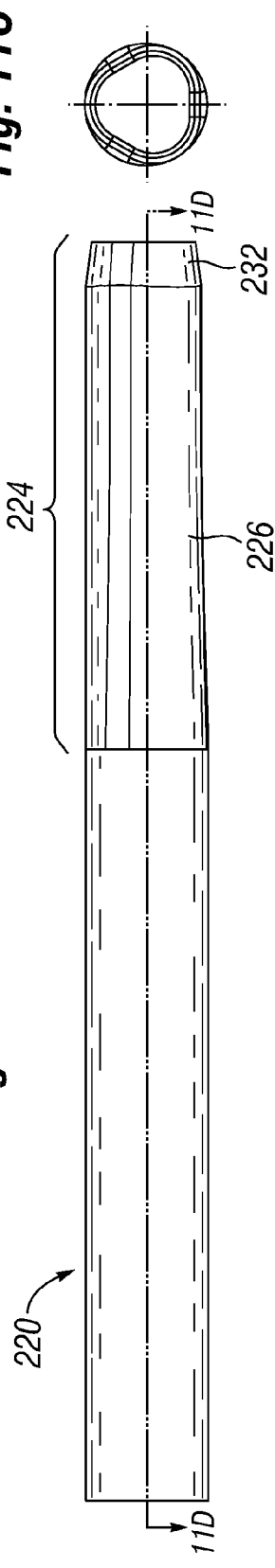
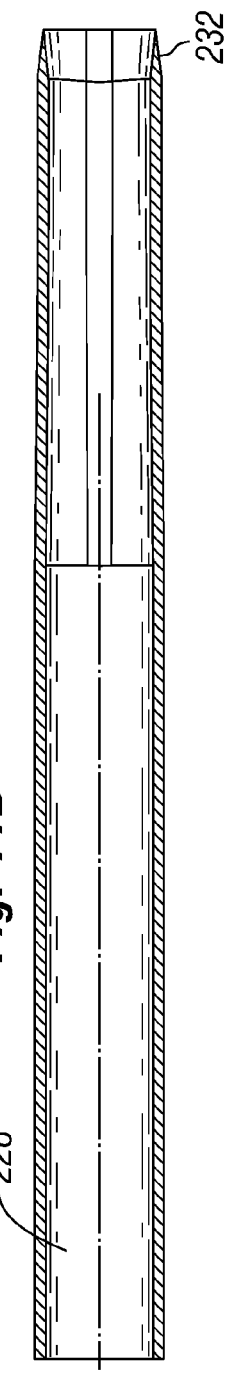

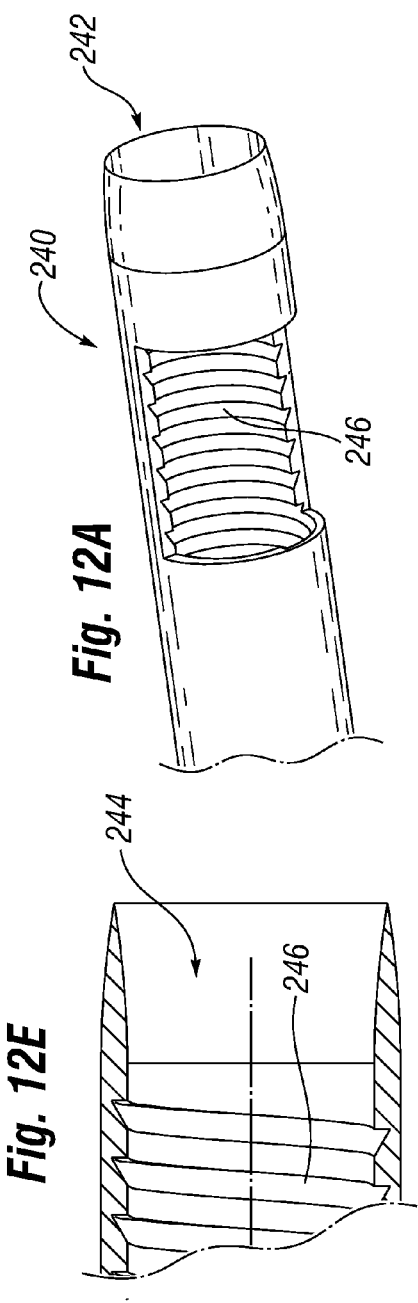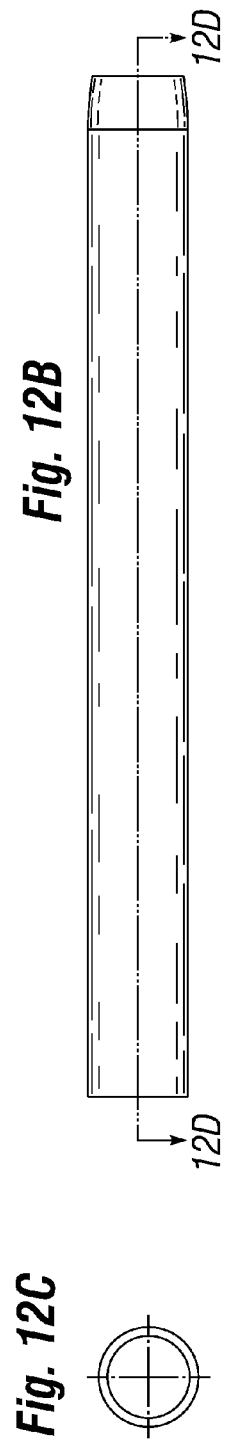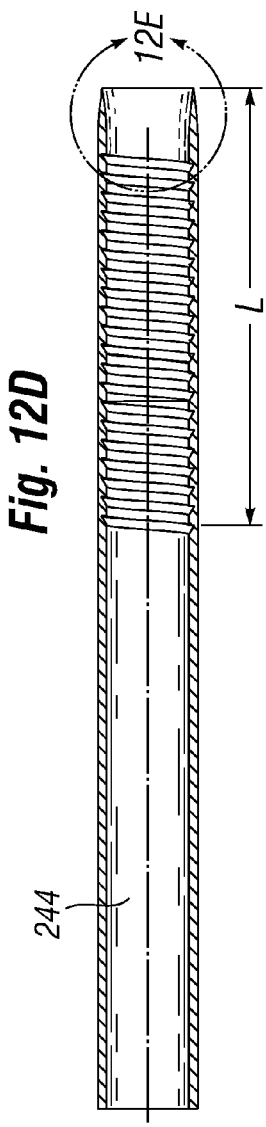
Fig. 12A
Fig. 12B
Fig. 12C
Fig. 12D
Fig. 12E

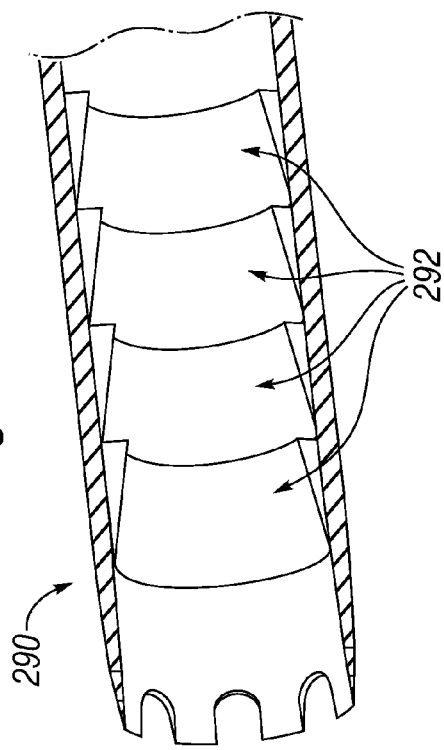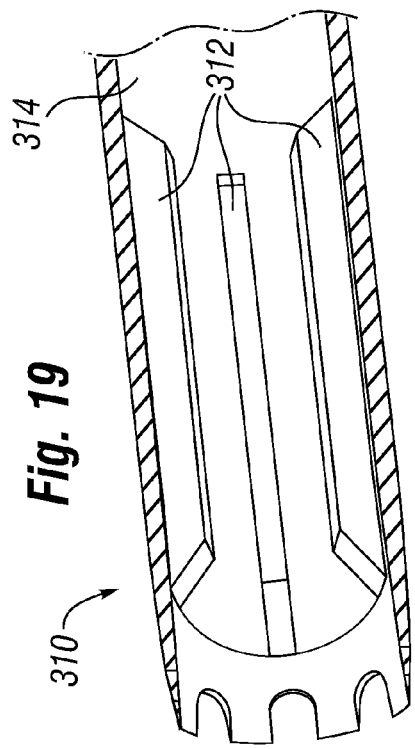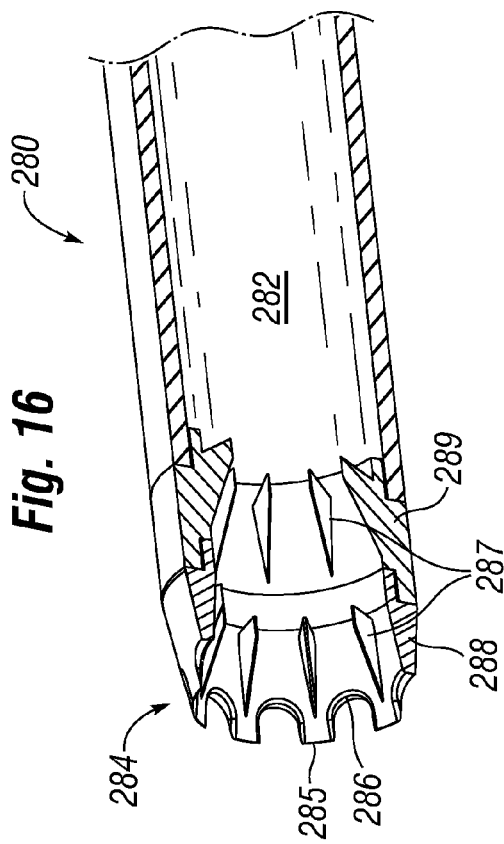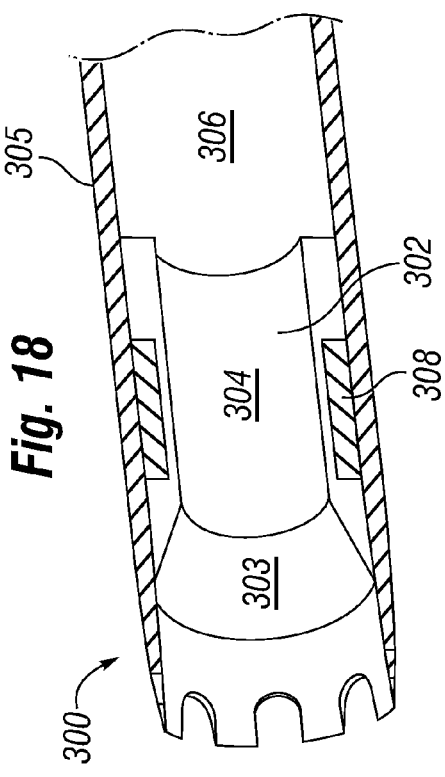

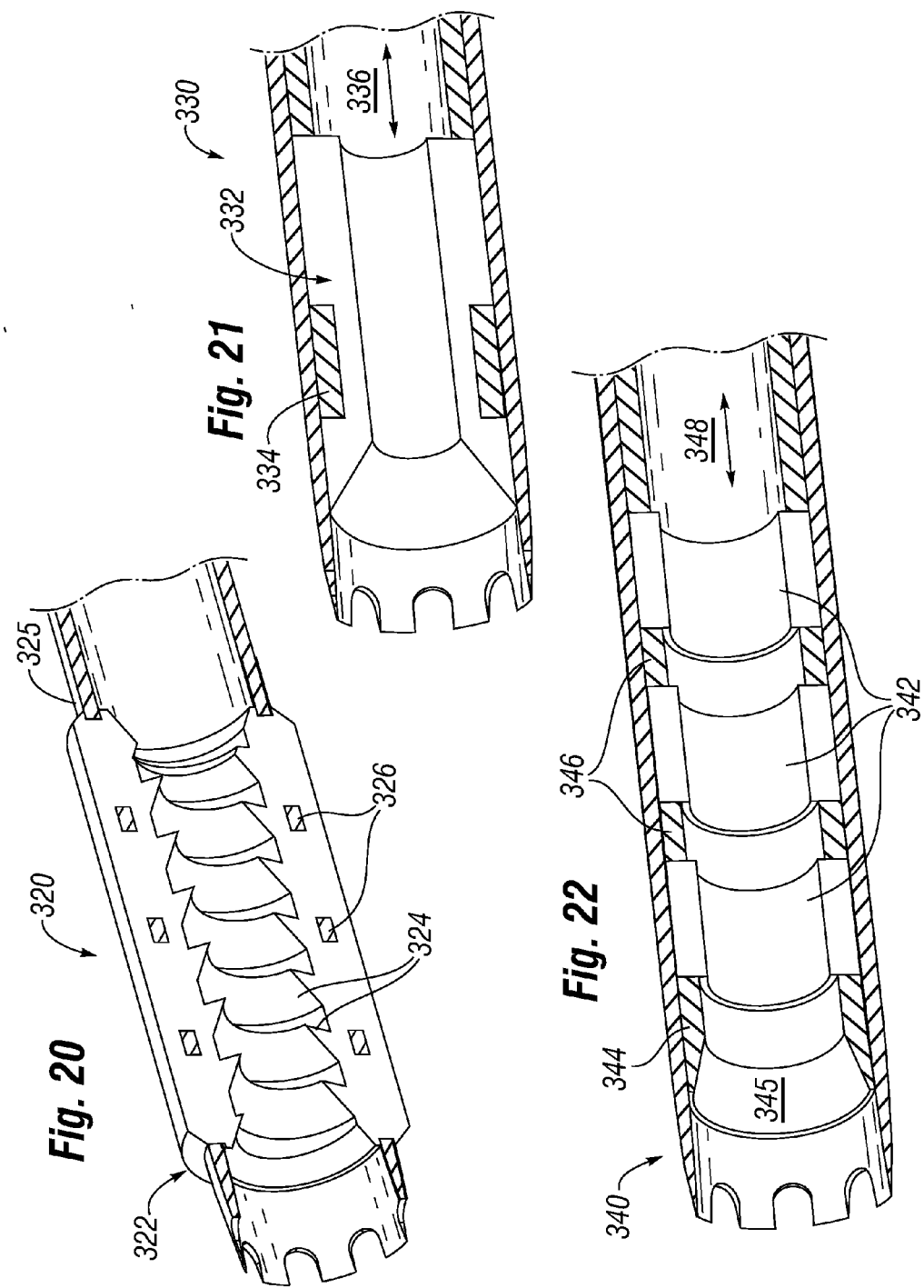

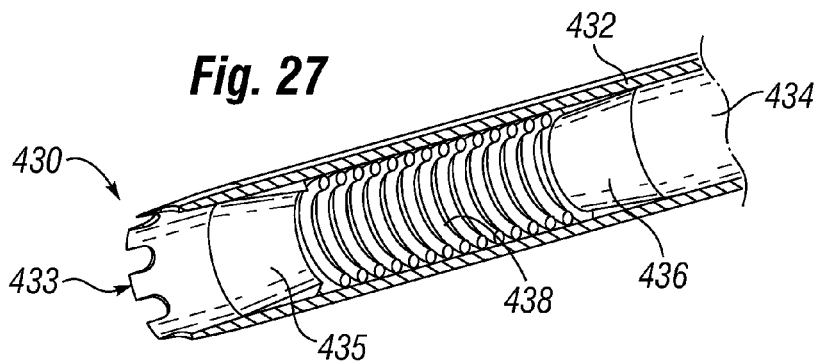
Fig. 27
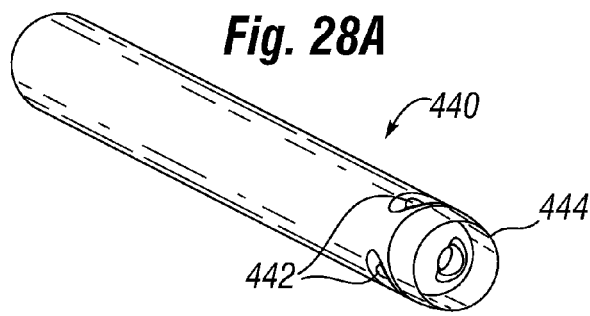
Fig. 28A
Fig. 28B
Fig. 28C
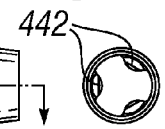
Fig. 28D
Fig. 29A
Fig. 29B
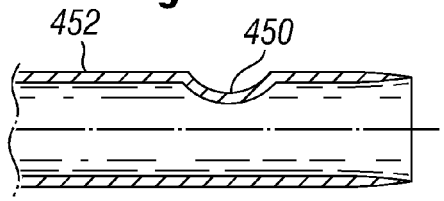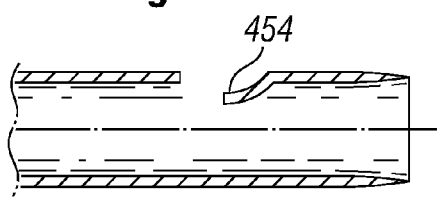

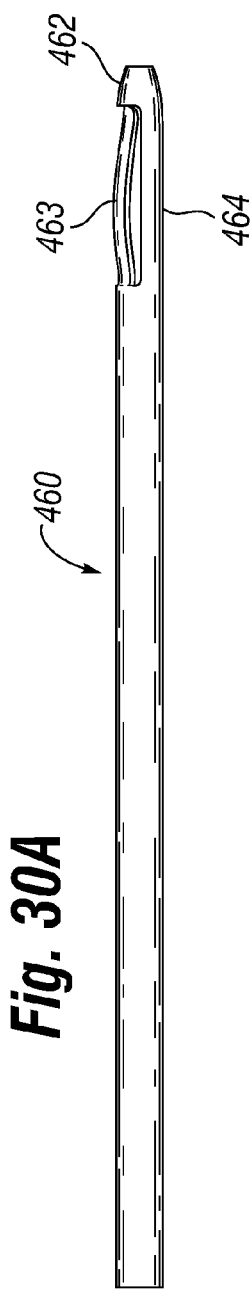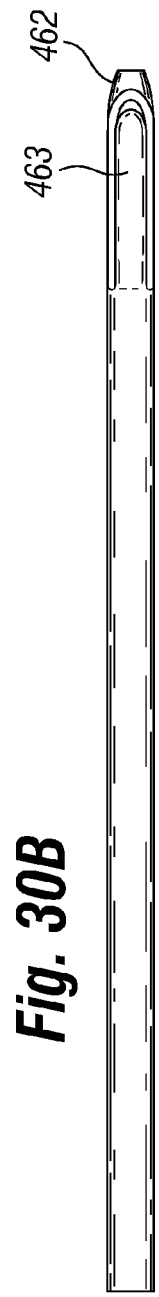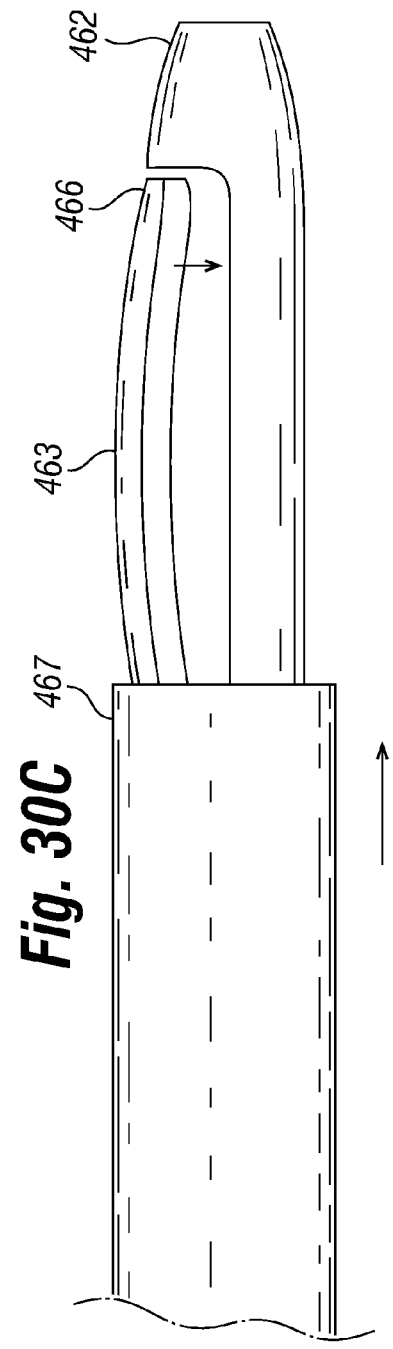

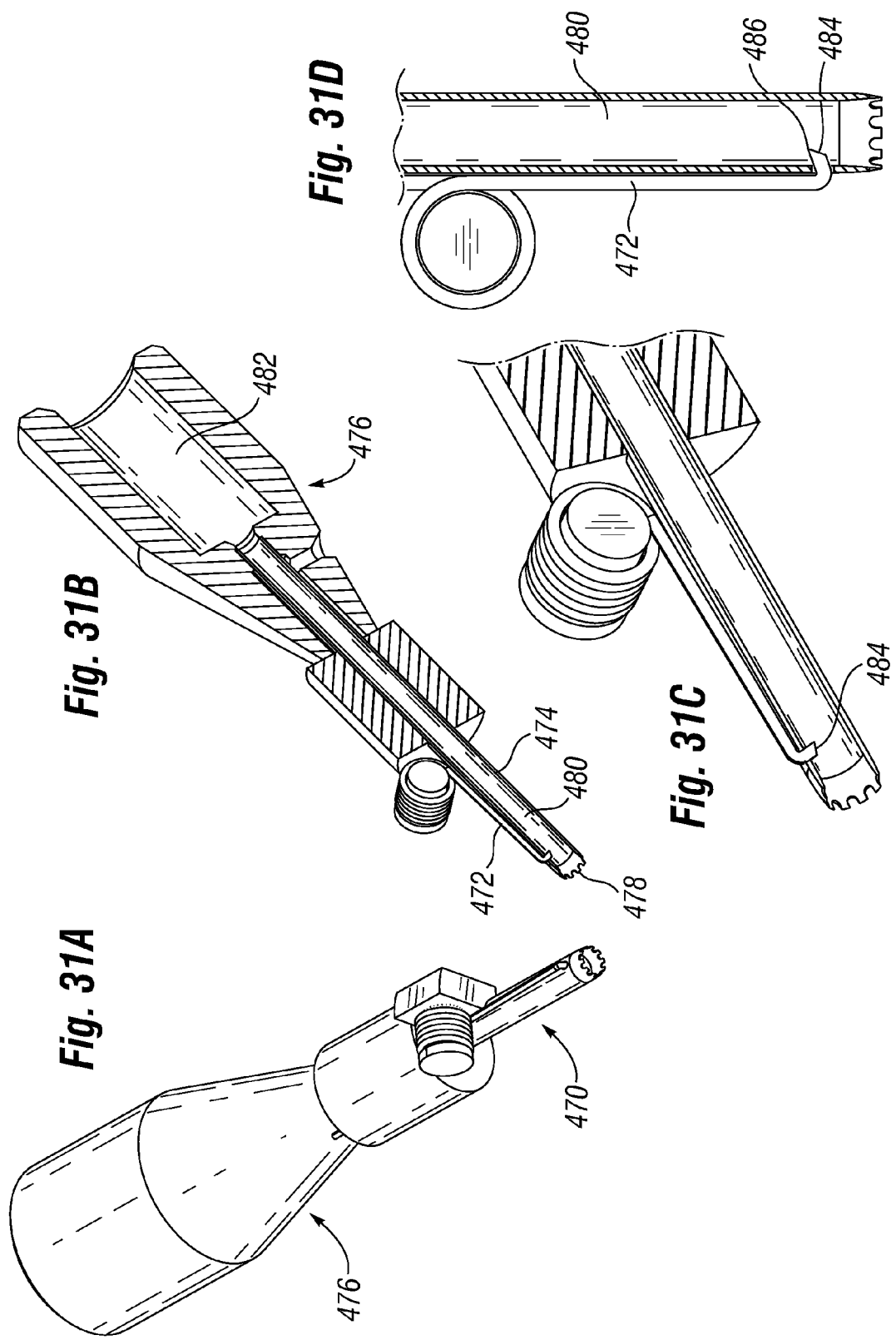

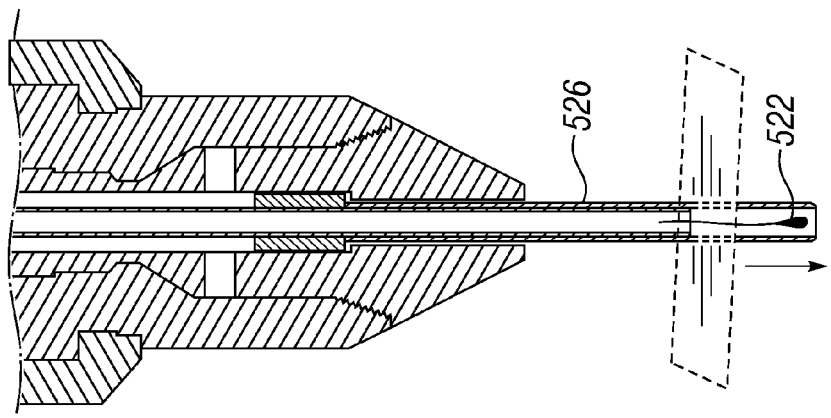
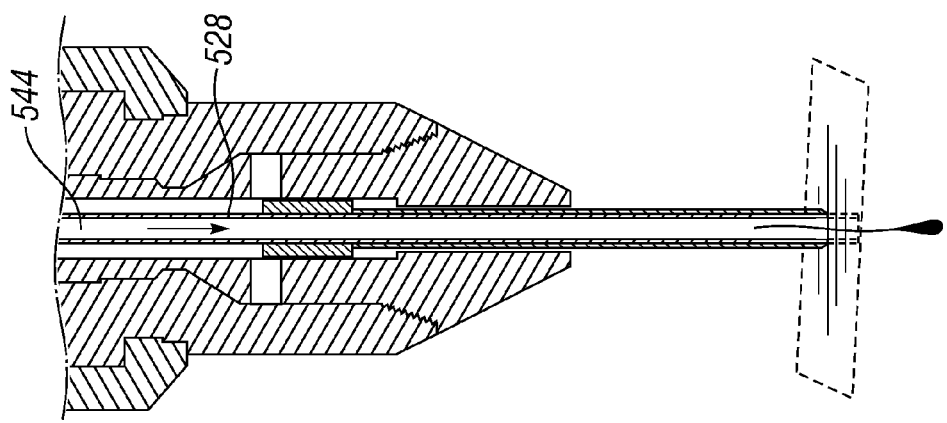
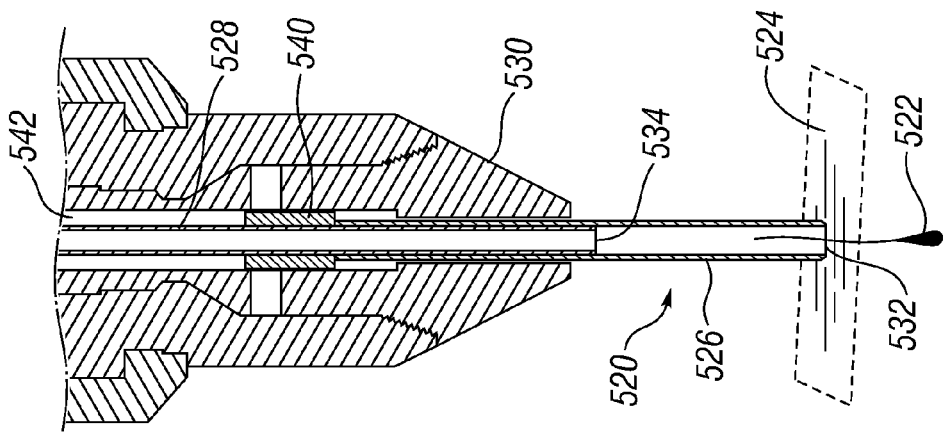

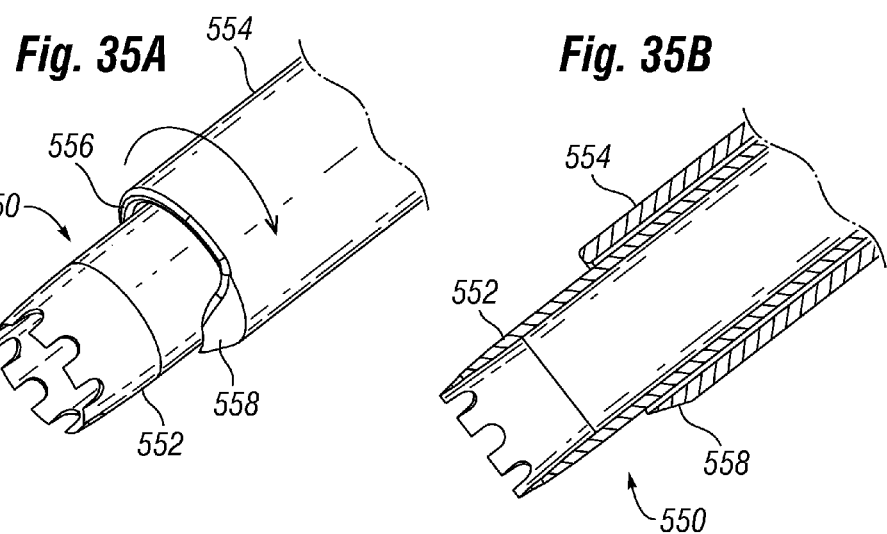
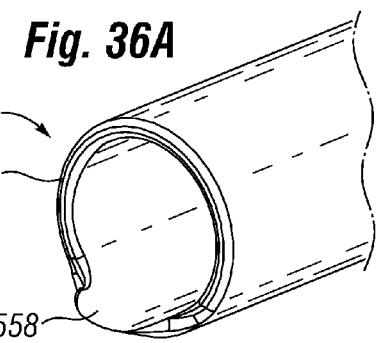
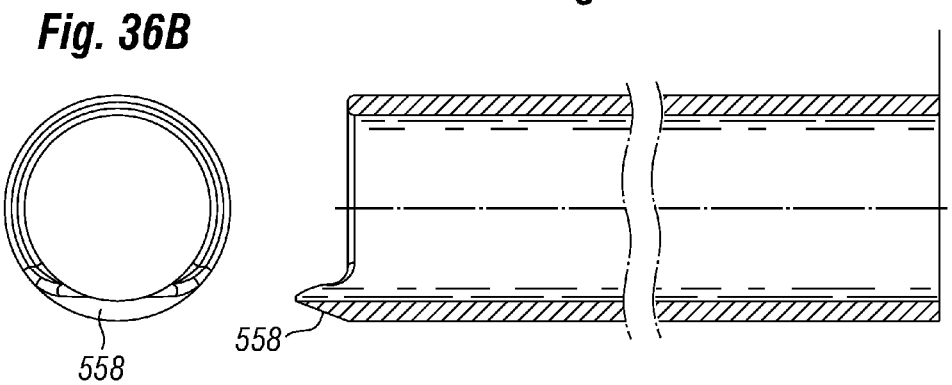

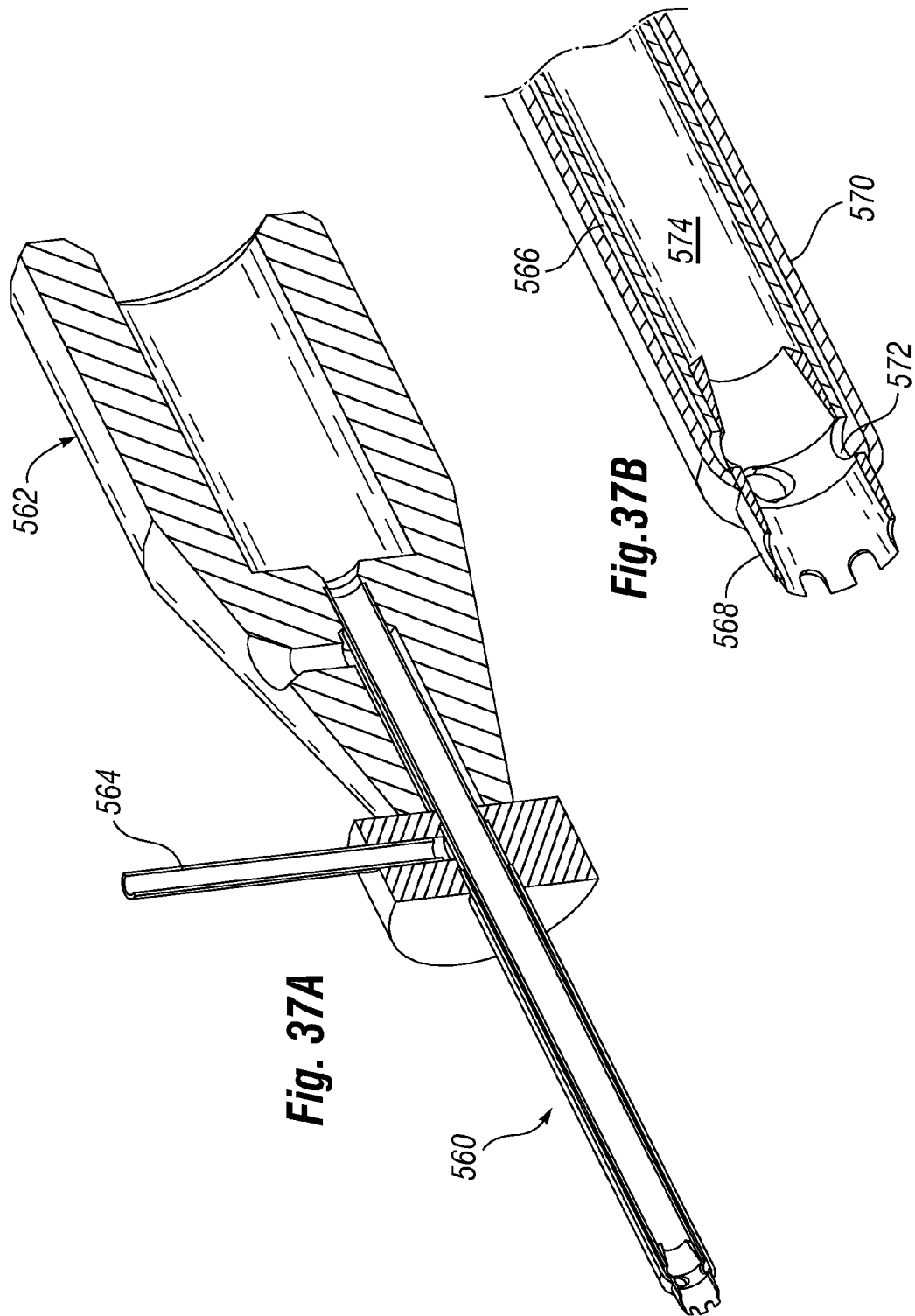

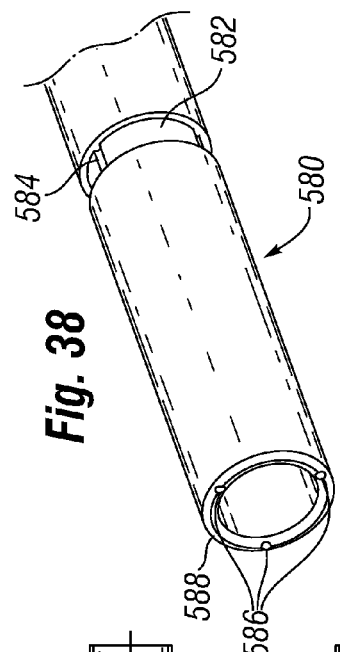
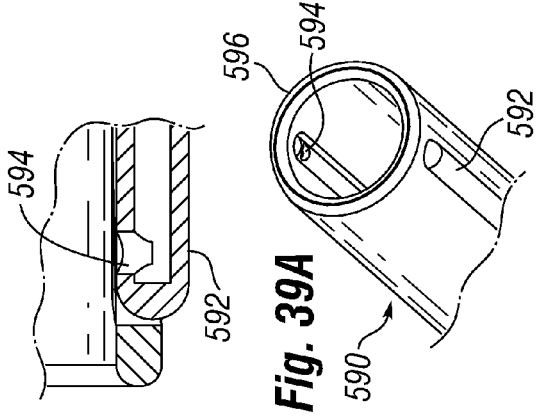
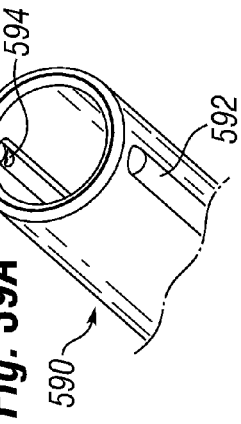
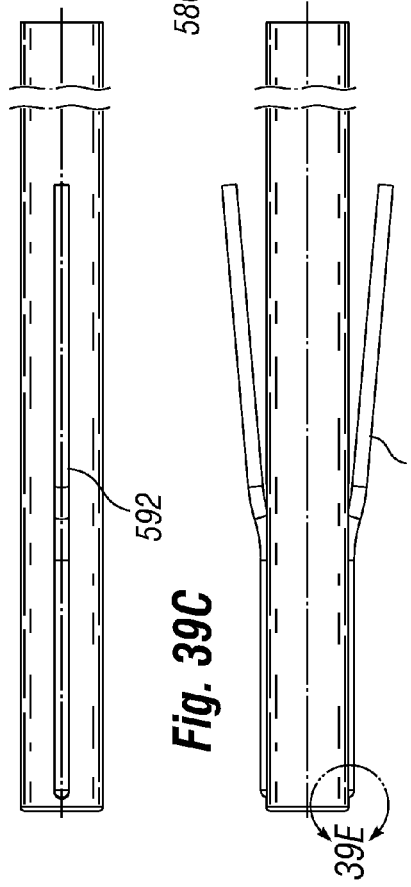
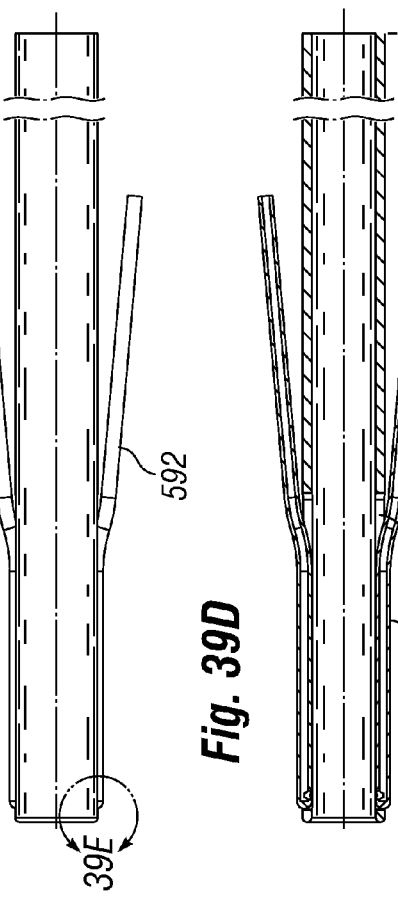
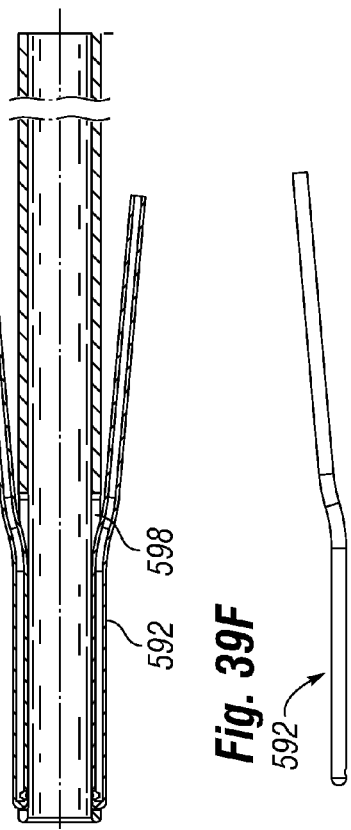

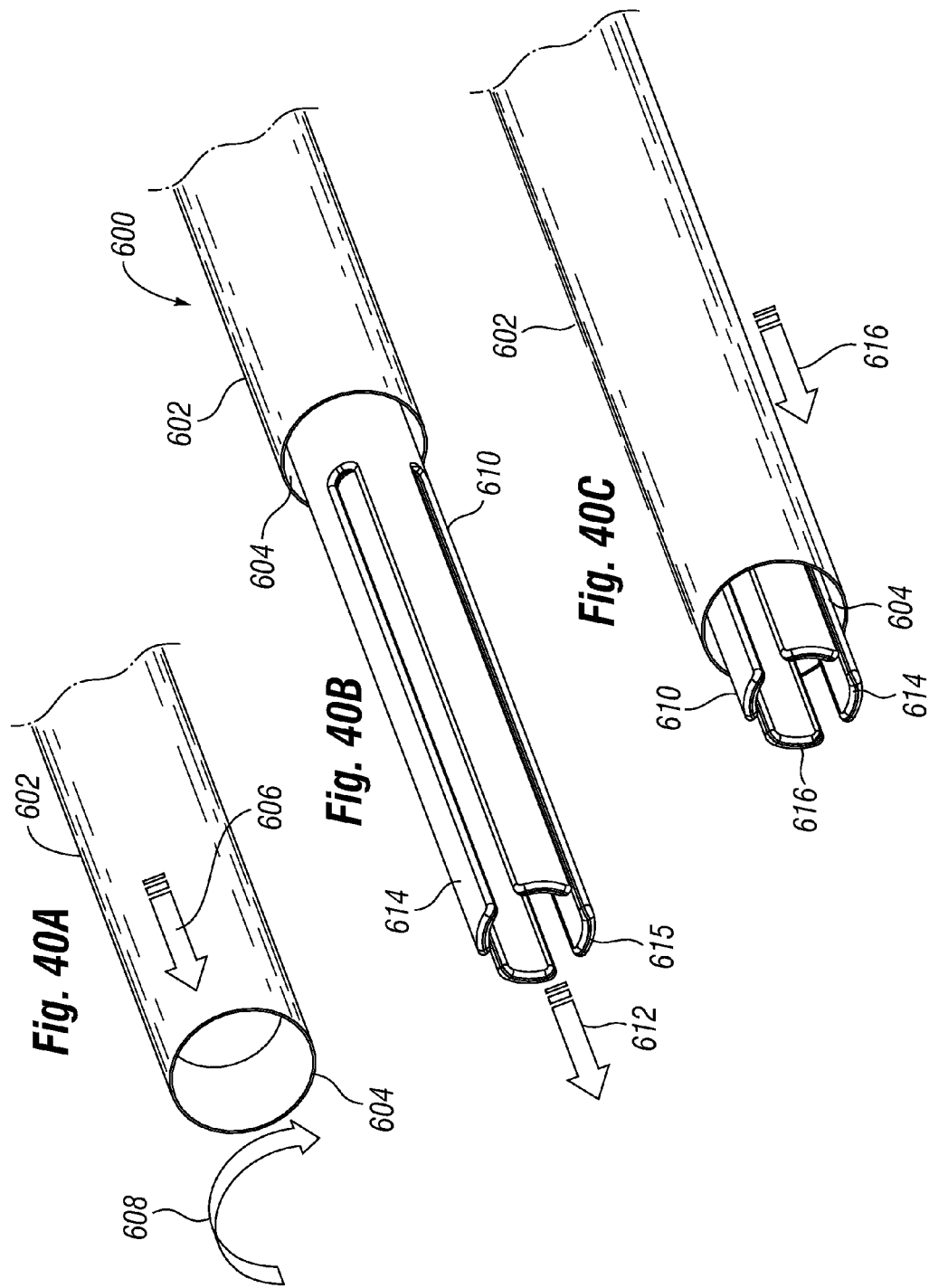

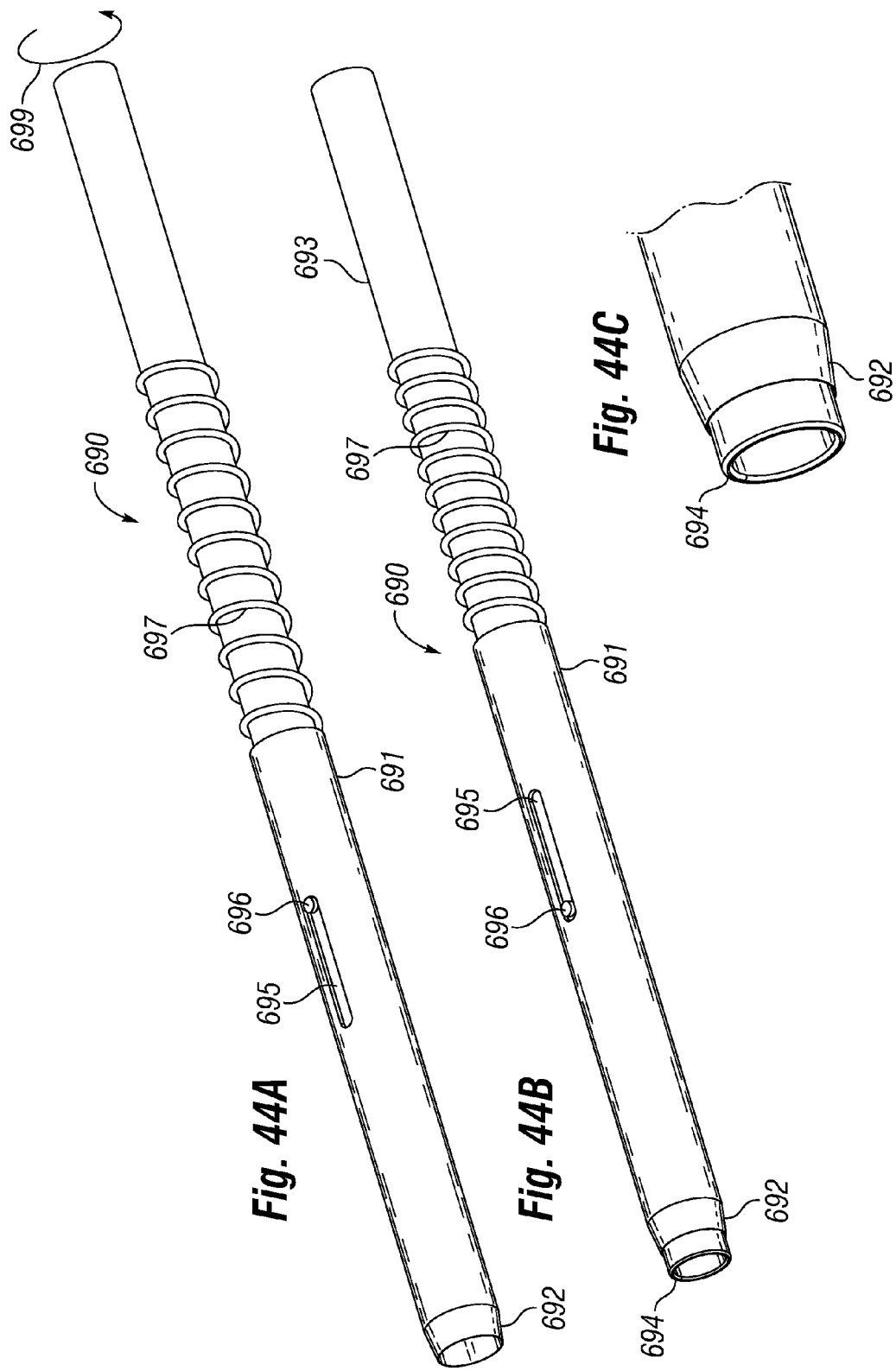

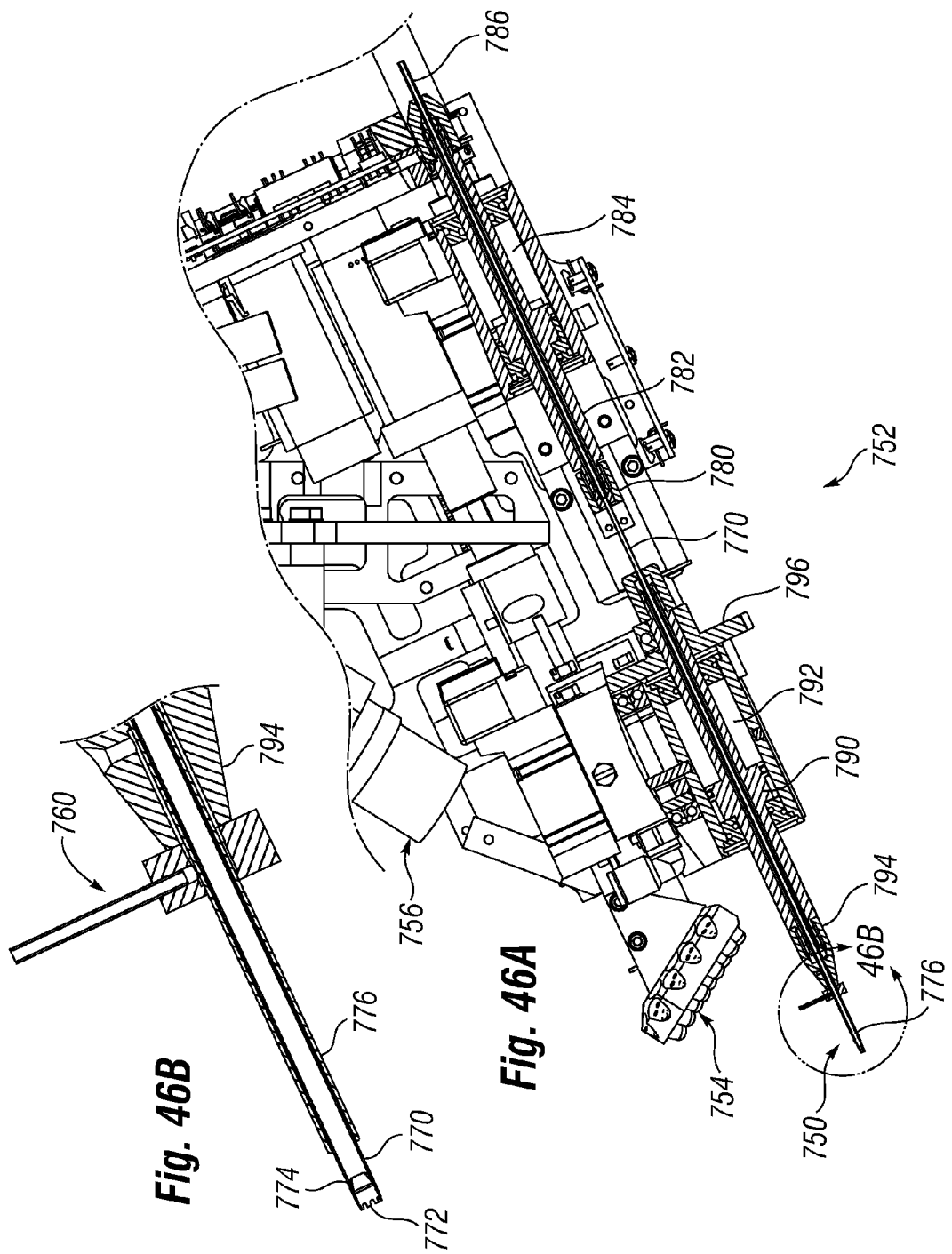

BIOLOGICAL UNIT REMOVAL TOOLS AND METHODS

RELATED APPLICATIONS

This application is a continuation application of co-pending U.S. patent application Ser. No. 13/409,834, filed on Mar. 1, 2012, which is a continuation of U.S. patent application Ser. No. 12/050,917, filed on Mar. 18, 2008 (issued as U.S. Pat. No. 8,133,237), which claims priority under 35 U.S.C. §119(e) to U.S. Provisional Application No. 60/895,530, filed on Mar. 19, 2007 and entitled DEVICES AND APPARATUS FOR HARVESTING FOLLICULAR UNITS.

FIELD OF THE INVENTION

This invention relates generally to tools used for the harvesting of various biological tissue samples, including hair follicles.

BACKGROUND OF THE INVENTION

There are various known tools and instruments for removing biological tissue samples from the body. For example, biopsy needles and punches are used when a small tissue specimen is required for examination, for example, to identify certain medical conditions. Another example of the biological tissue which is often desired to be removed or harvested is a hair follicle. Hair transplantation procedures are well-known, and typically involve harvesting donor hair grafts from the "donor areas," for example, side and back fringe areas of the patient's scalp, and implanting them in a bald area ("recipient area"). Historically, the harvested hair grafts were relatively large (3-5 mm), although more recently the donor grafts may be single "follicular units," which are naturally occurring aggregates of 1-3 (and much less commonly, 4-5) closely spaced hair follicles that are distributed randomly over the surface of the scalp. In one well-known process, a linear portion of the scalp is removed from a donor area by dissection, using a scalpel to cut down into the fatty subcutaneous tissue. The strip is then dissected (under a microscope) into the component follicular units, which are then implanted into a recipient area in respective puncture incisions made by a needle or razor blade. Forceps are typically used to grasp and place the follicular unit grafts into the needle puncture locations, although other instruments and methods are known for doing so.

In "Androgenetic Alopecia" (Springer 1996), M. Inaba & Y. Inaba disclose and describe a method for harvesting singular follicular units utilizing a hollow needle punch having a cutting edge and an interior lumen with a diameter of 1 mm, which is about equal to the diameter of critical anatomical parts of a follicular unit. The needle punch is axially aligned with an axis of a follicular unit to be extracted and then advanced into the scalp to cut the scalp about the circumference of the selected follicular unit. Thereafter, the follicular units are easily removed, e.g., using forceps, for subsequent implantation into a recipient site with a specially devised insertion needle. Sometimes, the sharp end of the needle punch cuts through, or transects, the hair shaft, rendering the follicular unit less than desirable. At other times, the incident angle at which the hollow punch contacts the skin surface causes the punch to stretch the skin and cut a relatively large flap of surrounding tissue along with the hair follicle, which may interfere with a subsequent implant procedure.

U.S. Pat. No. 7,172,604 (Cole) discloses an instrument for the extraction of individual follicular units. Several steps in a process disclosed in Cole for extracting a hair follicle from the skin are shown in FIGS. 1A-1C. FIG. 1 shows a section of skin 20 containing a hair follicle 22 with a hair 24 disposed therein, wherein a tubular harvesting punch 26 contacts the surface of the skin. The punch 26 contacts the skin at an angle with respect to the skin's surface over the location at which the hair 24 emerges from the skin. A sharp end of the punch 26 penetrates the skin and advances to a depth D of between about 0.05-0.5 millimeters. The surgeon then angles the punch 26 to an angle $\alpha_2$, shown in FIG. 1C, along the same axis as the hair growth, and further advances the punch into the dermis to a second depth $D_2$ of 2-7 millimeters.

Published U.S. Patent Application 20050267506 (Harris) discloses a method and apparatus for the extraction of follicular units by first scoring the outer skin layers with a sharp punch, removing the sharp punch, and then inserting a blunt punch into the incision to separate the hair follicular unit from the surrounding tissue and fatty layer to reduce the incidence of hair transection. Another U.S. Pat. No. 6,585,746 (Gildenberg) discloses a hair transplantation system utilizing a robotic system, including a robotic arm and a hair follicle end effector associated with the robotic arm that could be used to harvest hair follicles from the donor area.

To illustrate certain problems associated with the existing devices for removal of the biological tissue specimens, including specifically follicular unit harvesting, FIG. 2A shows the outline of a typical biological unit 30 removed from a body surface by a tubular harvesting cannula (not shown) advanced at an angle to the surface. The cannula generally removes a tissue plug 32, preferably centered in the example shown around a follicular unit having a bulb 34 and shaft 36. However, because the cannula advances into the skin at an angle, an undesirable lateral flap 38 of skin in the direction that the cannula is angled may result. This appendage or flap 38 occurs more often in high-speed punching using a harvesting cannula or needle and low angles of incidence from the body surface, such as between 15-45°. The flap 38 may interfere with movement of the biological unit 30 through the harvesting tool, its removal from the body surface and its retention in the removal tool. Moreover, in case of subsequent implantation of the harvested hair, the existence of the flap 38 interferes with the preference for small and closely spaced incisions at the implantation site. FIG. 2B shows an additional problem associated with the sliding of the cannula before a complete penetration of the skin while being advanced at an angle which results again in the creation of the flap and also in biological unit 30 being transected along the shaft 36. These two problems are typical reasons for discarding harvested biological units 30 used in hair transplantation, and may also be undesirable for biopsy or other applications where specimens of biological tissue need to be taken.

Despite certain advances in improving the tools for harvesting of biological tissue, there remains a need for a more efficient harvesting tool that increases the yield of usable harvested specimens, improves retention of the harvested units in the removal tool and the quality of the obtained specimens.

SUMMARY OF THE INVENTION

The present invention provides a number of solutions to deficiencies in the prior art and includes various features for increasing the yield of usable harvested biological specimens for instance a follicular unit, a skin sample, a tissue sample, or a biopsy unit. In general the invention provides tools that effectively penetrate tissue and remove and retain biological units therein without damaging them. One particularly useful application for the tools described herein is in the area of hair harvesting and transplantation, which requires the removal of countless follicular units. The tools can be manually operated or incorporated into an automated system, including robotic system.

In accordance with a first aspect, the present invention provides a method of removing biological tissue from a donor area comprising the steps of:
  a. rapidly advancing an inner elongated body to penetrate the donor area, the inner elongated body having a lumen sized to receive a biological unit and a distal tip adapted to cut through tissue;
  b. halting the advance of the inner elongated body at a first depth;
  c. relatively more slowly advancing an outer elongated body concentrically over the inner elongated body so that a distal tip of the outer elongated body extends past the first depth to a second depth, the distal tip of the outer elongated body being relatively duller than the distal tip of the inner elongated body; and
  d. withdrawing the inner and outer elongated bodies to remove the biological unit from the donor area.

The inner and the outer elongated bodies may be simultaneously withdrawn, or withdrawal of the inner elongated body may be initiated, for example, after the withdrawal of the outer elongated body is initiated. The method is desirably robotic comprising the use of a robotic system. In one embodiment, the outer elongated body advances into the donor area through an incision created by the distal tip of the inner elongated body, optionally while rotating the outer elongated body. The rotation of the outer elongated body may be slightly off the axis of the inner elongated body. In one embodiment, the distal tip of the outer elongated body defines a relatively circular periphery and a lip projecting distally therefrom, and the method comprises rotating the outer elongated body while it is advanced into the donor area so that the lip enters into and guides the rest of the periphery of the distal tip of the outer elongated body into the circular incision in the donor area created by the inner elongated body. Furthermore, a fluid or gas may be supplied under pressure to the distal tip of the outer elongated body.

Another aspect of the present invention is a method of removing biological tissue from a donor area comprising advancing an inner elongated body to penetrate the donor area, the inner elongated body having a lumen sized to receive a biological unit and a distal tip adapted to cut through tissue, advancing an outer elongated body concentrically over the inner elongated body so that a distal tip of the outer elongated body extends past the distal tip of the inner elongated body, supplying a fluid or gas under pressure to the distal tip of the outer elongated body, and withdrawing the inner and outer elongated bodies to remove the biological unit from the donor area. Fluid or gas may be delivered under pressure through one or more longitudinally extending channels each opening at a port located close to the distal tip, for example to sever the biological unit from surrounding tissue. Desirably, the method is substantially automated, and the biological unit is a follicular unit.

A still further exemplary method of removing biological tissue from a donor area of the present invention comprises:
  a. positioning a removal tool adjacent a donor area, the removal tool including an inner elongated body having a lumen sized to receive a biological unit and a distal tip adapted to cut through tissue, an outer elongated body, and a retention member adapted to contact the biological unit and impede its movement within the tool in a distal direction;
  b. advancing the inner elongated body to penetrate the donor area;
  c. advancing the outer elongated body concentrically over the inner elongated body so that a distal tip of the outer elongated body extends past the distal tip of the inner elongated body; and
  d. withdrawing the inner and outer elongated bodies to remove the biological unit from the donor area with assistance of the retention member.

In the aforementioned method the retention member may be radially movable such that the method includes radially displacing the retention member from a retracted position to a retention position. For instance, the retention member may be a balloon. Alternatively, the retention member comprises an elastic member positioned around the outer elongated body and having a portion that extends through a window in the outer elongated body. In another version, the retention member is axially movable, and the method includes axially displacing the retention member from a retracted position to a retention position. Still further, the retention member may be deformable so as to be deformed and surround the biological unit and constrict its movement in a distal direction.

A biological tissue removal tool in accordance with another aspect of the present invention comprises an inner elongated body having a lumen sized to receive a biological unit and a distal tip adapted to cut through a body surface, an outer elongated body axially concentrically movable over the inner elongated body and having a distal tip with a periphery, and a lip portion of the periphery that extends farther than the remainder of the periphery. The distal tip of the outer elongated body is preferably duller than the distal tip of the inner elongated body. The distal tip of the inner elongated body, the outer elongated body, or both may have an internal or external taper. In one embodiment, the lip portion is contoured to be streamlined against the inner elongated body.

A further biological tissue removal tool of the present invention includes an inner elongated body having a lumen sized to receive a biological unit, an outer elongated body axially movable concentrically over the inner elongated body, wherein one of the inner or outer elongated bodies has a distal tip for cutting through tissue, and a subsystem for dispensing fluid or gas to a distal tip of one of the inner or outer elongated bodies. Desirably, one or both of the inner elongated body and outer elongated body includes one or more longitudinally extending channels each opening at a port located close to the respective distal tip for delivering the fluid or gas to the distal tip. The one or more channels may be formed in a wall of the respective inner or outer elongated body, or are defined within a conduit that is mounted along a wall of the respective inner or outer elongated body. Preferably, one or both of the inner elongated body and the outer elongated body includes a plurality of ports circumferentially spaced around the distal tip thereof for delivering the fluid or gas to the distal tip.

In the exemplary tool with distal fluid or gas delivery, the distal tip of the outer elongated body may be suitable for cutting through tissue, and the inner elongated body includes a grasper defined by a plurality of circumferentially spaced fingers. Also, the tool may further incorporate a robotic mechanism for moving the inner and outer elongated bodies with respect to one another and actuating the fluid or gas dispensing subsystem. One of the inner or outer elongated bodies preferably has a distal end with a periphery comprising a combination of cutting segments for cutting through a body surface and relief segments for blunt dissection. In addition, a retention member adapted to contact the biological unit and impede its movement within the tool in a distal direction may be provided in the tool.

In another aspect of the present invention, a biological unit removal tool includes an inner elongated body having a lumen sized to receive a biological unit and a distal tip adapted to cut through a body surface, and an outer elongated body axially concentrically movable over the inner elongated body and having a distal tip. The outer elongated body defines at least one window in a side wall, and a plurality of elastic bands surrounds the outer elongated body at the window. The window is configured such that the elastic bands are biased inward and constrict around a biological unit positioned within the outer elongated body.

In an inflatable embodiment of the present invention, a biological unit removal tool includes an inner elongated body having a lumen sized to receive a biological unit and a distal tip adapted to cut through a body surface, and an outer elongated body axially concentrically movable over the inner elongated body and having a distal tip. The outer elongated body defines at least one window in a side wall, and includes an inflatable membrane positioned at the window. Inflation of the membrane causes it to expand radially inward through the window and constrict around a biological unit positioned within the outer elongated body.

In another embodiment of the present invention, a biological unit removal tool includes an inner elongated body having a lumen sized to receive a biological unit, and an outer elongated body axially concentrically movable over the inner elongated body and having a distal tip adapted to cut through a body surface. The inner elongated body includes a grasper defined by a plurality of circumferentially spaced fingers that is actuated by axial movement of the outer elongated body thereover.

An exemplary robotic system provided by the present invention includes a variety of relatively movable concentric tubes, such as inner and outer tubes, one of which has a distal tip adapted to cut through a body surface. A substantially automated mechanism includes separate actuators for the inner and outer tubes, preferably gas piston/cylinder actuators. The substantially automated mechanism also may include means for rotating at least one of the inner or outer tubes. Desirably, a fluid or gas delivery subsystem may be incorporated to deliver fluid or gas to the distal tip of one or both of the inner and outer tubes. A visualization subsystem may also be provided to monitor operation of the distal tip of the concentric tubes and transmit information to a display.

In another embodiment of the present invention, a biological unit removal tool includes an inner elongated body having a lumen sized to receive a biological unit, and an outer elongated body axially concentrically movable over the inner elongated body and having a distal tip adapted to cut through a body surface. The inner elongated body has a dull distal end used for blunt tissue dissection once the skin is initially pierced by the outer elongated body. The inner elongated body carries a spring member which applies a moderate axial force against the proximal end of the outer elongated body. The compliance of the spring is much less than that of a patient's skin tissue, so that the spring compresses as the outer elongated body presses against the skin surface.

In a further aspect of the present invention, a biological unit removal system includes a removal tool having concentric tubes, one of which has a distal tip adapted to cut through a body surface. The tool includes a retention member for impeding movement of a biological unit through a lumen of the tool in a distal direction. Optionally, a fluid delivery system may be provided to deliver fluid between the concentric tubes and to the distal tip of the tool.

In a still further exemplary embodiment, a follicular unit removal tool comprises an elongated body having a lumen sized to receive a follicular unit and a distal tip configured to penetrate a skin surface. One or more channels extend along the elongated body and open at a port located close to the distal tip for delivering a fluid or gas to the distal tip. The channel may be formed in a wall of the elongated body and opens at a distal end of the body. Alternatively, the channel is defined within a conduit that is mounted along a wall of the elongated body.

Another feature of the present invention described herein and useful with any of the specific structural embodiments is the application of a fluid/gas under pressure through ports at the distal end of the tool for severing connective tissue. For instance, a tool with channels described above may penetrate tissue and while rotating or retracting the fluid/gas may be directed under pressure from the ports. Not only does the direct physical contact of the fluid/gas help sever tissue bonds, but the pressure associated with such an infusion of fluid helps push the tool backward and thus break the connection of the biological unit with its surroundings. The tool may be rotated at the same time to help this process.

In further additional embodiments, a biological tissue removal tool of the present invention comprises an elongated body having a lumen sized to receive a biological specimen and a distal tip having both cutting and relief segments to avoid transection of the biological unit. In addition, the removal tool has discrete retention members located around the periphery of the lumen and in alignment with at least some of the relief segments. Desirably the relief segments are dulled while the cutting segments are relatively sharp.

Another aspect of the invention described herein which may be useful alone or in combination with other features is a removal tool having an elongated body with a non-circular radial cross-section. The non-circular shape may be a rounded polygon, such as a rounded triangle, and provides the tool with the ability to apply torque to a biological sample as the tool rotates to help extract it from its surrounding tissue connections.

It should be understood that the various retention features of the removal tools of the present invention can be used in combination with other features of the inventions described herein unless expressly mutually exclusive. For example, various described embodiments of the concentric inner and outer elongated tubes may be combined with one or more retention features and structures according to another aspect of the invention described herein. Similarly, the novel distal tips of the removal tool of the present invention can be incorporated into an inner or outer concentric tubes of the removal tool of the present invention. Likewise, various combinations of features can be incorporated into a manual, semi-automatic, or fully automated system. In short, unless stated otherwise, any combination of features described herein are contemplated.

Other and further objects and advantages of the invention will become apparent from the following detailed description when read in view of the accompanying figures.

BRIEF DESCRIPTION OF THE DRAWINGS

Features and advantages of the present invention will become appreciated as the same become better understood with reference to the specification, claims, and appended drawings wherein:

FIG. 2A shows the outline of a biological unit removed from a body surface by a harvesting tool advanced at an angle to the surface, while

FIGS. 3A-3E are various views of a biological unit removal tool having a distal relief segment in accordance with the present invention;

FIG. 4 shows the removal tool of FIG. 3 angled with respect to a body surface just prior to piercing the surface to extract a follicular unit;

FIGS. 4A-4B illustrate the surface footprint in a body surface made, respectively, by a conventional sharp-ended tubular removal tool and the tool of FIG. 3 of the present invention;

FIGS. 5A-5C are perspective and elevational views of another biological unit removal tool of the present invention having alternating relatively sharp and blunt segments on a distal tip;

FIGS. 6A-6D are perspective views of the distal tips of additional exemplary alternative biological unit removal tools of the present invention having various designs of alternating relatively sharp and blunt segments;

FIGS. 7A-7D are perspective and elevational views of another biological unit removal tool of the present invention having opposite sharp points separated by smoothly curved blunt segments;

FIGS. 8A and 8B are perspective views of two more embodiments of biological unit removal tools of the present invention having diametrically-opposed sharp segments separated by flat blunt segments;

FIGS. 9A-9D are perspective and elevational views of another exemplary biological unit removal tool of the present invention having diametrically-opposed relatively sharp segments separated by relatively flat blunt segments;

FIGS. 10A-10E are perspective views of the distal tips of alternative biological unit removal tools of the present invention having various designs of the alternating sharp and blunt segments;

FIGS. 11A-11D are perspective, elevational, and longitudinal sectional views of a further embodiment of the biological unit removal tool of the present invention having a non-circular radial cross-section to help retain a biological unit therein;

FIGS. 12A-12E are perspective, elevational, and longitudinal sectional views of a biological unit removal tool according to another aspect of the present invention having an internal retention member to help retain a biological unit therein;

FIG. 16 is a cutaway perspective view of a biological unit removal tool of the present invention having axially-spaced rows of discrete circumferentially-spaced retention members;

FIG. 17 is a cutaway perspective view of a biological unit removal tool of the present invention having axially-spaced rows of circumferentially continuous retention members;

FIG. 18 is a cutaway perspective view of yet another embodiment of the biological unit removal tool of the present invention having an internal retention member made, at least partially, of a non-traumatic material;

FIG. 19 is a cutaway perspective view of a biological unit removal tool of the present invention having elongated discrete circumferentially-spaced retention members;

FIG. 20 is a cutaway perspective view of a further embodiment of the biological unit removal tool of the present invention provided with an internal retention member made of deformable material;

FIG. 21 is a cutaway perspective view of another biological unit removal tool of the present invention having an exemplary internal retention member formed of a deformable material and including an actuating member for deforming the retention member;

FIG. 22 is a cutaway perspective view of a further embodiment of the biological unit removal tool of the present invention having an alternative internal retention member formed of a plurality of spaced deformable rings;

FIG. 27 is a cutaway perspective view of a biological unit removal tool of the present invention having a combination of internal retention members therein;

FIGS. 28A-28D are perspective, elevational, and sectional views of a still further biological unit removal tool of the present invention featuring internal retention dimples;

FIGS. 29A and 29B illustrate two stages in an exemplary process for forming an internal retention member of the present invention;

FIGS. 30A-30C are elevational views of a further alternative biological unit removal tool of the present invention in which a bendable finger is formed in a sidewall;

FIGS. 31A-31D are perspective and sectional views of an alternative biological unit removal tool of the present invention illustrating another embodiment of the present invention comprising a spring-loaded retention finger;

FIGS. 34A-34C are longitudinal sectional views of three stages of operation of an embodiment according to another aspect of the present invention directed to a concentric tube concept for the biological unit removal tool;

FIGS. 35A and 35B are perspective and sectional views of the distal end of another exemplary embodiment of a concentric tube biological unit removal tool of the present invention wherein an outer tube includes a leading extension;

FIGS. 36A-36C are perspective, elevational, and sectional views of the exemplary outer tube of the removal tool of FIG. 35;

FIG. 37A is a perspective sectional view of an exemplary concentric tube biological unit removal tool embodiment of the present invention mounted at the distal end of a holding mechanism that incorporates a fluid delivery system;

FIG. 37B is an enlarged view of the distal end of the system of FIG. 37A, showing ports for fluid delivery and an internal retention member;

FIG. 38 is a perspective view of the distal end of an outer tube of the removal tool that may be used in a modified version of the system of FIG. 37A, and which incorporates longitudinal fluid delivery ports;

FIGS. 39A-39F are perspective, elevational, and sectional views of an exemplary biological unit removal tool embodiment of the present invention incorporating separate conduits that provide fluid or gas flow ports to the distal end thereof;

FIGS. 40A-40C are perspective views of another exemplary embodiment of the concentric tube biological unit removal tool of the present invention with an outer tube and a split inner tube for retaining biological units;

FIGS. 44A-44C are perspective views of a concentric tube biological unit removal tool of the present invention with a spring between inner and outer elongated bodies;

FIGS. 46A and 46B are perspective views of yet another embodiment of the biological unit removal tool incorporated in the exemplary robotically-operated system for hair removal and implantation.

DETAILED DESCRIPTION OF THE PREFERRED EMBODIMENTS

Figure 1A:
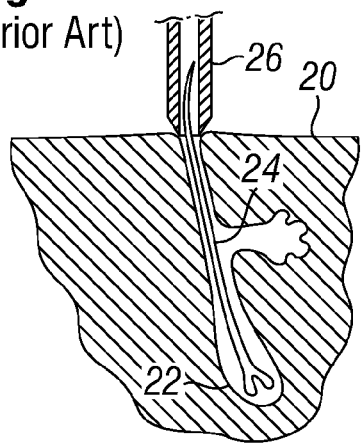
FIGS. 1A-1C show a section of skin containing a hair follicle in contact with a portion of a tool of the prior art.
Figure 1B:
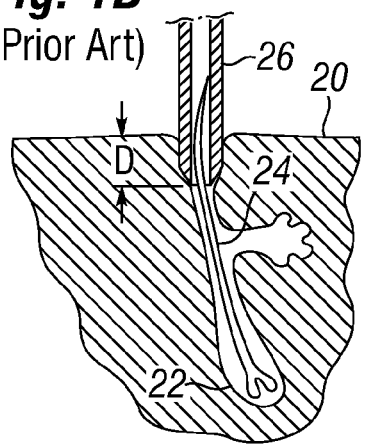
Figure 1C:
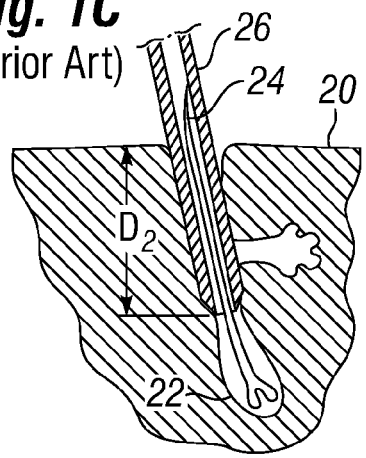

In the following Detailed Description, reference is made to the accompanying drawings that show by way of illustration some exemplary embodiments in which the invention may be practiced. In this regard, directional terminology, such as "top," "bottom," "front," "back," "distal," "proximal," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated systems described herein may also be robotically-assisted or computer/software/machine-instruction controlled. The devices and methods of the present invention are useful in manual procedures and systems, as well as in automated procedures and system. The tools of the present invention could be used with the robotically-assisted systems and procedures. The adverb "automatically" when referring to use of a particular component of a system or a particular step in a process means that such step is accomplished autonomously, i.e., without real-time manual assistance.

The term "tool" or "biological unit removal tool" as used herein refers to any number of tools or end effectors that are capable of removing or harvesting various biological tissues, for example, follicular units ("FUs") from a body surface. In general, however, the tools of the present invention may be useful for removing biological units other than FUs from a body surface. In this sense, a body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The distal end of removal tools (for example, punches, coring devices, cutting and/or trimming devices, needles), are typically sharpened, to cut and extract the tissue (e.g., hair follicle).

Various embodiments of follicular unit harvesting cannulas (or tools) described herein may be employed in harvesting systems, whether such systems are fully-automated (e.g., robotically controlled), semi-automated, or manually controlled. It will be appreciated by those skilled in the art that each harvesting cannula design may have certain benefits (e.g., superior retraction and retention of follicular units, less trauma to the surrounding skin and tissue), or drawbacks (e.g., complex design and/or operation, higher manufacturing costs, increased trauma), relative to the other embodiments. Thus, selection of a particular harvesting cannula distal end design will depend on the particular performance criteria sought to be achieved.

"Biological units" include discrete units used in cosmetic, diagnostic, and dermatological procedures, for example, various tissues, including that extracted for biopsies or grafting, fat units, skin units, etc. Examples of the biological units particularly useful with the present invention are hair grafts, or follicles, or "follicular unit(s)." Other biological units may be tissue used for diagnosis of cancer, such as from the areas of the breast, liver, prostate, colon and small bowel, or lungs. Other tissue examples where biopsies are performed include bone, heart and brain tissue. Furthermore, "biological unit" may alternatively be referred to as "biopsy sample," "biopsy specimen," "biological tissue sample," or "biological tissue specimen."

As mentioned above, the term biological units encompasses a number of things, though the present invention is particularly useful in hair harvesting, to provide devices and methods for harvesting follicular units (FUs). As such, the term follicular units (or FUs) will be used herein simply as an example for purposes of describing some embodiments of the present invention with the understanding that it represents more broadly biological units.

Exemplary Distal Tip Designs of Biological Unit Removal Tools

Figure 2A:
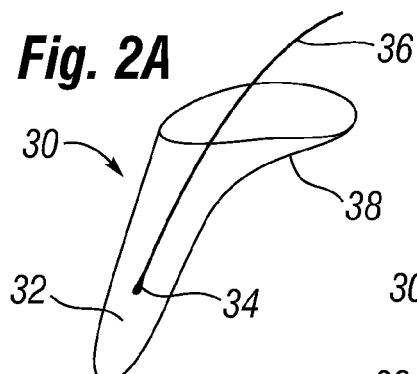
Figure 2B:
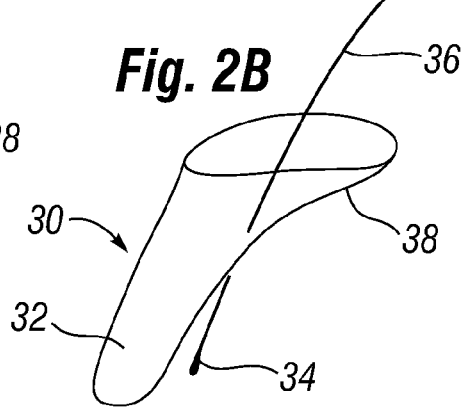
FIG. 2B shows the same biological unit and the resulting hair transection.

According to the first aspect of the present invention, biological tissue removal tools are provided with certain distal tip designs that help to minimize damage to the harvested biological unit and to improve the quality of the harvested specimen. The below described embodiments substantially reduce or completely eliminate creation of a flap 38 as explained in reference to FIGS. 2A-B of the background section. FIGS. 3A-3D show various views of a biological unit removal tool 40 having an elongated body 42 extending between a proximal end 44 and a distal tip 46. In the most common embodiment as illustrated, the elongated body 42 comprises a constant diameter defining a cylindrical lumen 48 therein. For use as a follicular unit harvesting tool, the elongated body 42 may have a length L of about 4 to 25 mm, and a diameter of about 0.5 to 1.5 mm, although these dimensions will vary depending on the application.

As best seen in FIGS. 3C and 3E, the periphery of the distal tip 46 includes a relatively sharp segment 50 primarily for cutting tissue and a relief segment 52. Desirably, a shallow taper 54 formed in the wall of the elongated body 42 narrows from a maximum dimension and circumferential line 56 to a minimum dimension at the distal tip 46. The circumferential line 56 thus defines a proximal end of the taper 54. The relief segment 52 is recessed or offset proximally from the distal-most sharp segment 50, and simply because of its different axial location may be less sharp because of the tapered wall thickness and thus less able to cut through tissue. Alternatively, the relief segment 52 may be formed with an even more blunt (e.g., rounded) or dull edge than the sharp segment 50. As seen in FIG. 3C, the relatively sharp segment 50 extends at least 50% around the periphery of the distal tip 46, and preferably it extends around about 75% of the periphery. Generally, sharp or cutting segments are capable of cutting through epidermis, dermis and subcutaneous fat layers of skin.

The biological unit removal tool 40 advantageously helps improve the yield of usable biological units, in particular follicular units for hair transplantation. More particularly, FIG. 4 shows the tool 40 advancing toward a body surface BS at an angle of incidence α. Preferably the tool 40 has been centered over and angled toward an exposed hair shaft 58. The tool 40 is oriented with the relief segment 52 disposed at the lowermost point around the distal tip 46 and the sharp segment 50 on top. Because of the recessed angle of the relief segment 52, and its more blunt leading edge, severance of the body surface BS is delayed in comparison with a completely all around sharp distal tip.

To better illustrate the advantages of the tool 40, FIGS. 4A-4B illustrate the surface footprint in the body surface BS made, respectively, by a conventional sharp-ended tubular removal tool and the tool 40 of FIG. 3. As seen in FIG. 4A, a circular and sharp-ended tubular removal tool will tend to cut an elliptical footprint 60 around the hair shaft 58, resulting in the aforementioned flap 38 from FIG. 2A. FIG. 4A shows a dashed arcuate contact line 62 representing the point at which the relief segment 52 of the tool 40 will contact the tissue. Because of its blunt nature, the relief segment 52 tends to create a jagged or swallowtail trailing edge 64 in the body surface BS, as seen in FIG. 4B. Most of the material that results in the undesirable flap 38 has thus been removed. Furthermore, because the relief segment 52 is somewhat dull or blunt, there is less likelihood that it will transect the hair shaft 58 if the tool 40 is slightly mis-aimed or misaligned.

FIGS. 5A-5C illustrate another biological unit removal tool 70 of the present invention comprising an elongated body 72 extending from a proximal end 74 to a distal tip 76. The elongated body 72 is preferably tubular having an inner bore or lumen 78 extending from the proximal end 74 to the distal tip 76. In this regard, the distal tip 76 desirably defines a circular periphery, although the periphery may be non-circular as seen in an alternative embodiment below.

As shown best in FIG. 5A, the elongated body 72 features a distal taper 80 having a maximum thickness at its proximal end 82 and a minimum thickness at the distal tip 76. A series of alternating cutting and relief segments 84, 86 define distal tip 76. The cutting segments 84 jut farther in the distal direction than the relief segments 86, and desirably the distal taper 80 converges to a knife edge at the cutting segments 84. In an exemplary embodiment as illustrated, the periphery of the distal tip 76 resembles a crown with the cutting segments 84 defining ridges and each of the relief segments forming troughs 82 between two cutting segments. Moreover, the cutting segments 84 and the relief segments 86 may alternate around the periphery of the distal tip 76 in a repeating pattern with constant spacing, although as seen below the spacing may vary. It should also be noted that all or just some of the relief segments 86 may be offset proximally from the cutting segments 84. For instance, some of the relief segments 86 may be offset while others are at the same axial location but just not sharp. Also, the relief segments 86 may all be offset to the same location, or some may be offset more than others.

Because the relief segments 86 are recessed (offset proximally) relative to the cutting segments 84, they are located proximal from the convergence of the distal taper 80 and thus have a relatively larger wall thickness than the cutting segments. This can best be seen in FIG. 5C which looks at the distal facing elements of the removal tool 70. The wall thickness of the elongated body 72 equals the difference between its nominal OD and ID, whereas the exemplary knife edge of the cutting segments 84 is shown as a circular line and the radial thickness of the relief segments 86 is in between. In one possible configuration, the distal taper 80 extends linearly from its proximal end 82 to the distal tip 76, and the radial wall thickness of the relief segments 86 relative to the wall thickness of the elongated body 72 depends on their axial depth X and the length Y of the taper. For example, the elongated body 72 may have an OD of 0.066 inches (1.67 mm) and an ID of 0.054 inches (1.37 mm), such that the nominal wall thickness is 0.006 inches (0.15 mm). As the ratio X/Y increases, the radial thickness of each relief segment 86 increases proportionally. In the illustrated embodiment, the ratio X/Y is about ⅓, and therefore the radial thickness of each relief segment 86 is about 0.002 inches (0.051 mm). Of course, the distal taper 80 may be other than linear resulting in a different relationship between the depth of each relief segment 86 and its wall thickness. Desirably, for example, when used for follicular unit harvesting, the elongated body 72 OD ranges between 0.030-0.070 inches (0.7-1.8 mm), while the ID ranges between 0.020-0.040 inches (0.5-1.0 mm). The axial length Y of the distal taper 80 ranges between 0.030-0.060 inches (0.8-1.6 mm), and the depth X of each of the relief segments 86 ranges between 0.020-0.040 inches (0.5-1.0 mm). However slightly larger or smaller dimensions are also possible. For biopsy or other such general uses, the ID may increase, for example, up to about 0.06 inches (1.5 mm), with a corresponding OD increase to about 0.08 inches (2.0 mm).

In the context of hair transplantation, the inner diameter (ID) of the various tool lumens described herein are suitable for receiving follicular units, which, as mentioned, are naturally occurring aggregates of 1-3 (and much less commonly, 4-5) closely spaced hair follicles. For instance, the luminal diameter may range between 0.5-1.5 mm, and preferably is about 1.0 mm.

As mentioned, the alternating cutting segments 84 and relief segments 86 may circumscribe the periphery of the distal tip 76 in a repeating pattern with constant spacing. Of course, variable spacing without a repeating pattern may be used as well. The circumferential dimension of the cutting segments 84 may be equal to that of the relief segments 86 or it may be different. In the illustrated embodiment of FIGS. 5A-C, there are ten "ridges" or cutting segments 84 alternating with ten of roughly the same width "troughs" or relief segments 86, such that each of the cutting segments and relief segments spans an arc of about 18° around the longitudinal axis of the tool 70. More precisely, the relief segments 86 desirably span a slightly greater arc than the cutting segments 84. For instance, the distance between adjacent cutting segments 84 may be 0.010 inches (0.254 mm), and with the above exemplary dimensions for the diameter of the elongated body 72, the span of the each relief segment 86 is about 19°, while the span of each cutting segment 84 is about 17°. It should be understood, however, that the relative width of the segments 84, 86 as well as their spacing may vary, as will be seen below with respect to the alternative embodiments of FIGS. 6A-6D.

Likewise, the shapes of the cutting segments 84 and relief segments 86 may take a variety of forms. In the embodiment illustrated in FIGS. 5A-5C, each of the relief segments 86 includes generally axially-oriented sidewalls which transition to a semi-circular proximal end at the bottom of the trough. Because of the distal taper 80, the sidewalls of each relief segment 86 (corresponding to the sidewall of the adjacent cutting segments 84) tapers from a relatively thick proximal end to a minimum thickness at the distal tip 76.

FIGS. 6A-6D illustrate several alternative embodiments of the "crown-shaped" distal tips of biological unit removal tools of the present invention.

In FIG. 6A, a removal tool 90 features a distal tip 92 with six relief segments 94 separating four relatively narrow cutting segments 96 and two longer cutting segments 98. Three relief segments 94 are closely spaced on one side and diametrically opposed from the other three relief segments. The relief segments 94 and narrow cutting segments 96 closely resemble the shape and size of the segments 84, 86 described above, while each longer cutting segment 98 spans approximately 45° around the distal tip 92.

FIG. 6B illustrates a removal tool 100 having a distal tip 102 defined by a regular and repeating pattern all alternating relief segments 104 and cutting segments 106. The relief segments 104 are somewhat shallower and extend around a greater arc than the relief segments 86 described above. In an exemplary embodiment, the tool 100 has an OD of about 0.066 inches (1.67 mm) and an ID of 0.054 inches (1.37 mm), such that the nominal wall thickness is 0.006 inches (0.15 mm). However, each relief segment 104 spans 0.015 inches (0.38 mm) from side-to-side, or an arc about 29°, while each cutting segment 106 spans an arc only about 7°. Furthermore, though each relief segment 104 is somewhat shallower than that described above, its maximum wall thickness is equal to the embodiment described in FIGS. 5A-5C, preferably about 0.02 inches (0.51 mm). In this regard, a distal taper 108 may be non-linear so as to be more pronounced toward the distal tip 102.

FIG. 6C illustrates a still further biological unit removal tool 110 with a crown-shaped distal tip 112 featuring alternating cutting segments 114 and relief segments 116. In this embodiment the cutting and relief segments 114, 116 are again regularly and repeatedly spaced, though in contrast to the version of FIGS. 5A-5C there are only eight cutting segments 114 that are approximately equal in width to eight relief segments 116. In an exemplary embodiment, the tool 110 has an OD of about 0.050 inches (1.27 mm) and an ID of 0.042 inches (1.07 mm), such that the nominal wall thickness is 0.004 inches (0.10 mm). Each relief segment 116 spans a circumferential distance of 0.009 inches (0.23 mm), or just more than 22°, and the cutting segments 114 likewise span an arc of just more than 22°.

Finally, FIG. 6D illustrates a removal tool 120 having a distal tip 122 that includes six cutting segments 124 alternating with six relief segments 126. In this embodiment, the cutting segments 124 are relatively wider than the relief segments 126. Specifically, if the tool 120 has an OD of about 0.050 inches (1.27 mm) and an ID of 0.042 inches (1.07 mm), then the nominal wall thickness is 0.004 inches (0.10 mm). Each of the relief segments 126 centered at 60° apart from each other has a circumferential width of 0.010 inches (0.254 mm), or about 25°, and the cutting segments 124 span an arc of about 35°.

Providing alternating relatively sharp or cutting segments with relatively dull or relief segments reduces the chance of transection of hair shafts during follicular unit removal, as described above with respect to FIG. 2B. That is, the cutting segments perform the task of piercing tissue, but the distal tips described above also include the relief segments which bluntly dissect tissue. As the exemplary biological unit removal tools 70, 90, 100, 110, or 120 pass through tissue adjacent a follicular unit, for example, a hair shaft may be encountered by one of the leading cutting segments. As the tool proceeds, and before sufficient force is applied to sever the hair shaft, the shaft may migrate around the circumference of the tool into one of the relief segments. Thereafter, the removal tool continues downward into the tissue along the affected hair shaft rather than transecting it. The relative sizes and shapes of the cutting segments and relief segments determines the character and magnitude of cutting versus bluntly dissecting. For example, in some instances a tool that has less cutting ability may be required, such as when harvesting follicular units from a subject that has relatively thin hair follicles which transect more easily, and vice versa.

FIGS. 7A-7D represent another biological unit harvesting cannula or removal tool 130 of the present invention having a distal tip 132 defined by diametrically opposed cutting segments 134 having sharp points separated by smoothly curved blunt relief segments 136. Stated another way, the removal tool 130 has a parabolic-shaped distal end, including opposing cutting tips 134 and flat distal-facing edges 136. This design provides a more "blunted" distal end (due to the flat facing edges 136) for when the cannula 130 is being moved in a forward-plunging motion through the tissue after skin penetration, but still provides sharpened cutting edges 134 for cutting as the cannula 130 may be simultaneously rotated about its axis for the initial skin penetration. As with any of the harvesting cannula embodiments, the cannula 130 may be manufactured from stainless steel hypodermic tubing, and the tips of the cutting edges 134 may be chemically sharpened, if so desired.

FIGS. 8A and 8B are perspective views of two more biological unit removal tools of the present invention having diametrically-opposed sharp cutting segments separated by flat blunt segments.

FIG. 8A depicts a removal tool 140 having an outside-beveled tip 142 defining a pair of generally axially-extending cutting elements 144 separated by a pair of opposing slots 146. The slots 146 may be cut such that the sides 148 of the cutting elements are tapered distally (as shown in FIG. 8A), although it is not necessary that they taper. For example, the sides 148 of the respective cutting elements 144 taper to respective flat top surfaces 149.

The harvesting tool 140 may be manufactured, by way of example, from stainless steel hypodermic tubing (e.g., 304 SST, 16.5 Gauge) in accordance with well-known manufacturing techniques. The slots 146 in the distal tip 142 are preferably made after the tip has been beveled. In exemplary embodiments, the slots may be approximately 0.02 in to 0.04 in wide at their base (along the circumference of the cannula tip 102), and have a depth varying from approximately 0.01 in to 0.04 in. The side edges 148 and distal facing surfaces 149 of the cutting elements 144 may be chemically milled to increase their sharpness, if desired, or they may be dulled to reduce the potential for transecting the hair follicle(s) as the cannula is pressed into the cutaneous and subcutaneous tissue layers, as explained herein. The sides of the cutting elements 144 may be linear, as shown in FIG. 8A, but in alternative embodiments can have a more gradual, curved transition and/or a more shallow depth.

As will be appreciated by those skilled in the art, a sharper distal facing (or "leading") edge on the removal tool 140 will more easily pierce the epidermal without causing collateral damage, but a duller leading edge will reduce the chance of cutting (transecting) the portion of the hair follicle lying beneath the skin surface in the epidermal, dermal, and subcutaneous fatty tissue layers. In particular, the hair follicles will often extend at an angle in the cutaneous and subcutaneous tissue and, thus, a blunt harvesting cannula may "push" the hair follicle and surrounding tissue into its inner lumen, whereas a sharpened cannula my transect and thus destroy the follicle. Thus, potential design choices may incorporate aspects of both sharp initial skin penetration, and dull subcutaneous (below the skin surface) tissue dissection.

FIG. 8B depicts a further modification in which a biological unit removal tool 150 has opposing slots 152 removed from an inside-beveled tip 154, thus forming a pair of opposing cutting elements 156 extending axially from the distal end of the tool. The cutting elements 156 desirably have axially-extending side edges 157, though like the previous embodiment the slots 152 may optionally be cut such that the resulting cutting elements 156 have an inward sloping taper leading to their respective flat distal surfaces 158. It will be appreciated by those skilled in the art that the harvesting cannulas or tools 140 and 150 may be manufactured from the same type of tubing, e.g., stainless steel hypodermic tubing or other appropriate material, such as Titanium or Nitinol. The slots 152 in the tip 154 of tool 150 are preferably made after the tip has been beveled and may have a variety of dimensions.

FIGS. 9A-9D are perspective and elevational views of another biological unit removal tool 160 of the present invention having a distal tip 162 defined by diametrically-opposed cutting segments 164 separated by relatively flat relief segments 166, similar to those in FIGS. 8A and 8B. The removal tool 160 defines an external distal taper 168 that results in a sharp edge at the distal end of the cutting segments 164. Because of the taper 168, the relief segments 166 have a wall thickness and are thus somewhat blunt and less able to cut through tissue than the cutting segments 164.

As can be seen in the alternative embodiments of FIGS. 10A-10E, the configuration of the distal tip 162 can vary a great deal. However, in the exemplary embodiment shown in FIGS. 9A-9D, the tool 160 has a length L of between 0.67-1.5 inches (17.0-38.1 mm), an OD of about 0.062 inches (1.6 mm) and an ID of 0.052 inches (1.3 mm), such that the nominal wall thickness is 0.005 inches (0.13 mm). The distal taper 168 has a length A of about 0.03 inches (0.76 mm) and an angle θ with respect to the tool axis of about 5-10°. Each relief segment 166 has an axial depth B of about 0.01 inches (0.25 mm) and a circumferential span S of about 0.04 inches (1.0 mm). Each relief segment 166 has substantially rectangular profile preferably with bottom corners rounded to a radius r of about 0.005 inches (0.13 mm).

FIGS. 10A-10E are perspective views of the distal tips of alternative biological unit removal tools of the present invention having alternating relatively sharp and blunt segments similar to FIGS. 9A-9D. In some of these embodiments a distal taper begins proximally with respect to relief segments, like in FIGS. 9A-9D, while in others the distal taper is relatively short and thus begins distal to the relief segments.

FIG. 10A shows a removal tool 170 having elongated relief segments 172 that extend proximally past a distal taper 174. With this configuration, the wall thickness at the bottom of each of the relief segments 172 is the same as wall thickness of the tool 170.

FIG. 10B shows a removal tool 180 also having elongated relief segments 182, and an extremely short external distal taper 184. The side edges of the U-shaped relief segments 182 are rounded to further reduce their cutting ability.

FIG. 10C shows a removal tool 190 which is configured similar to the tool 180 of FIG. 10B, although diametrically-opposed relief segments 192 are about half as short in their axial dimensions.

FIG. 10D shows a removal tool 200 configured much like the removal tool 160 of FIG. 9A in that a distal tip 202 includes an external taper 204 and a pair of diametrically opposed cutting segments 206 separated by intermediate relief segments 208. However, the relief segments 208 are substantially deeper than the relief segments 166 described above, though remain within the tapered region 204.

FIG. 10E shows a removal tool 210 having a short external taper 212 leading to opposed cutting segments 214. The cutting segments 214 extend farther circumferentially around the tool 210 than previous embodiments, so as to define a pair of narrow relief segments 216. For example, the relief segments 216 may each span a circumferential arc of about 50°, while the cutting segments 214 each span an arc of about 130°. The tool 210 provides substantially more relative cutting edge than previous embodiments, but retains the ability to receive and protect a hair follicle in the relief segments 216.

The above-described various distal tips of the removal tool of the present invention could be used in combination with other features and aspects of additional inventions described below. For example, "crown-type" distal tips could be combined with various retention features and structures described herein for improving retention of the harvested specimen. Similarly, the novel distal tips of the removal tool of the present invention could be incorporated into an inner or outer cannula of the concentric tube removal tool as further described herein with reference to additional aspects of the present invention.

Biological Unit Retention Members

Many concepts of the present invention are designed to help retain a biological unit within a removal tool without damaging it. That is, the removal tool penetrates a body surface, causes a biological unit to enter a lumen therein, and then removes it. It is important that the biological unit goes with or is retained within the removal tool as it is retracted. Often, however, the biological unit remains connected in some manner to the tissue that had been surrounding it. For example, a follicular unit may remain attached to the body surface by surrounding connective tissue, even if a vacuum is used in the tool lumen. The surrounding connective tissue tends to pull back the follicular unit from the removal tool which sometimes results either in tearing the follicular unit apart, or simply not retaining it in the removal tool. Likewise, biological specimens that are taken for cancer biopsies, etc. share similar issues with follicular units. That is, it may be important to keep a biopsy specimen intact and not damaged or separated because it may be desirable to see all of the layers of the specimen in exact original order and form to determine an exact location of the cancerous portion (or other problem). The present invention thus provides a number of retention solutions that help pull biological units free from the surrounding tissue.

Moreover, the present invention provides improved biological unit removal tools that solve certain problems associated with some prior art designs that have one or two sharp proximally-oriented barbs to retain tissue specimens with a tool. Such barbs tend to either destroy or damage the specimen, and may in any event have insufficient retention structure to hold the biological unit within the tool upon removal. In contrast, the present invention provides a number of retention structures that are effective in retaining the biological unit within the lumen of the tool without damaging the biological unit.

A first biological unit removal tool or cannula 220 having retention structure is seen in FIGS. 11A-11D, in which a distal end 222 is non circular in shape. The cannula 220 has a transitional section 224 in which a wall 226 and inner lumen 228 of the cannula 220 transitions from having a generally circular cross-section at 230 to the non-circular distal tip section 222. The cannula 220 further includes a distal taper 232 that could be formed by either one or both internal and external tapers as seen in FIGS. 11B and 11D. In use, the cannula 220 is pushed axially forward to pierce the skin and cannulate the cutaneous and subcutaneous tissue surrounding a targeted follicular unit. The cannula 220 may then be rotated, thereby more easily separating the captured portion of tissue from the tissue bed, since the non-circular shape prevents the cannula from simply rotating around the encapsulated tissue without separating its base from the underlying tissue bed. In the illustrated embodiment, the non-circular distal tip section 222 has a rounded triangular shape. It should be understood that other rounded polygons, such as squares, hexagons, and the like, could be used instead. An exemplary rounded triangular shape is considered effective in applying torque to the biological unit within the lumen 228, which is therefore transferred to the connective tissue between the biological unit and its surroundings. Furthermore, the non-circular shape can be combined with any of the other retention members described herein, as opposed to using a tubular distal section.

FIGS. 12A-12E depict still another embodiment of a tubular harvesting cannula 240 having a sharpened, e.g., beveled, distal tip 242, and an internal helical retention member to help retain a biological unit therein. As revealed by the cut-away portion of FIG. 12A, an inner wall of a cannula lumen 244 includes a series of grooves 246 to entrap tissue. The grooves 246 may be provided as a helical spiral, a series of concentric rings, or some other geometric pattern, and act to "grab" and retain the tissue surrounding a follicular unit. The tip 242 may vary in sharpness, depending on how it is inserted through the skin and tissue, e.g., depending on its speed of forward trajectory through the skin surface, whether it is being rotated, the speed of rotation, etc. In one exemplary embodiment, the axial length L of the series of grooves 246 comprises less than 50% of the entire length of the biological unit removal tool 240. In a particularly preferred embodiment, the tool 240 has a length of about 0.67 inches (17.0 mm), while the length L of the series of grooves 246 is about 0.29 inches (7.4 mm).

In other embodiments of the retention members described below with reference to FIGS. 13-24, the axial length of the retention member will depend on the length of the biological unit to be removed. For example, with reference to follicular units, the corresponding retention member used with the tool for follicular unit removal may be as little as about 0.5 mm and as long as about 8 mm. In some preferred embodiments, the total axial length of such retention member (whether it is a single retention feature or a combination of several rows of the retention features) may range between about 2-5 mm. Also, it is preferred that the retention member be located somewhat near the distal end of the removal tool for more effective retention. For example, a distal end of the retention member may be located immediately proximally and up to about 3 mm from the distal end of the removal tool. The tool 240 may be a stainless steel hypotube, and the grooves 246 may be machined onto the inner surface thereof such that they do not project inward beyond the ID of the tube.

In use, once the distal end of cannula 240 is fully inserted through the skin and "screwed" into the tissue surrounding a follicular unit, the cannulated tissue expands into the grooves 246. The cannula 240 is then withdrawn, thereby tearing the captured follicular unit from the surrounding body tissue. A "reverse" rotational motion may be required to dislodge the captured follicular unit from the cannula 240. For example, an internal obturator may be used to push the follicular unit back out the distal cannula opening 242, while the cannula 240 is simultaneously rotated in a reverse direction of rotation than was used to capture the follicular unit, thereby "unscrewing" the follicular unit from the cannula lumen 244.

Figure 13:
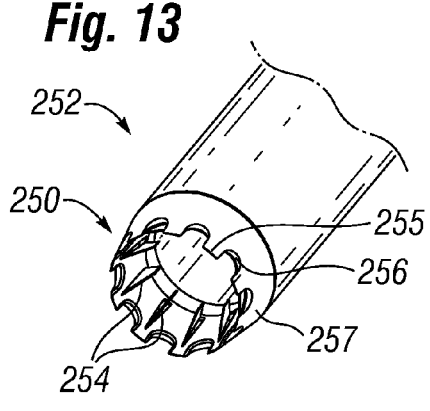
FIG. 13 is a perspective view of an exemplary distal tip of a biological unit removal tool of the present invention having a plurality of discrete retention members disposed at least substantially around an internal circumference thereof.

FIG. 13 illustrates the distal tip 250 of a biological unit removal tool 252 of the present invention having a plurality of discrete retention members 254 disposed at least substantially around an internal circumference thereof. The distal tip 250 is configured similar to the distal tip 76 shown in FIG. 5A, with alternating cutting and relief segments 255, 256. The retention members 254 are located within a distal tapered region 257, preferably aligned with each of the leading-edge cutting segments 255. In illustrated embodiment, there are ten such cutting segments 255 each centered 36° apart from one another. Therefore, in a preferred embodiment corresponding to this example with ten cutting segments, there are ten retention members 254 evenly spaced 36° apart from one another. However, it should be understood that a plurality of retention members disposed at least substantially around an internal circumference of the distal tip 250 is also possible, and could encompass, for example, a minimum of four retention members, which may be evenly spaced 90° apart, or may be distributed in two diametrically-opposed pairs each spaced less than 90° apart. The odd number of the above-described retention members is also within a scope of the present invention.

In the exemplary embodiment, the retention members 254 comprise thin axially-oriented blades or vanes angled in a proximal direction so as to permit movement in a proximal direction of a biological unit into the tool, but impede movement in a distal end direction from the lumen of the tool 250. As will be seen below, the discrete retention members 254 may take a variety of forms, and may not be discrete members but alternatively form a continuous surface around the internal circumference of the particular removal tool. In this regard, distributed discrete retention members may also be replaced with a single retention member that has a non-constant radial cross-section around its periphery.

As mentioned above, the exemplary removal tools solve certain problems associated with some prior art designs that have one or two relatively sharp proximally-oriented barbs to retain tissue specimens with a tool. Namely, the discrete retention members 254 are designed to retain a biological unit within the lumen of the tool without damaging the biological unit. This is accomplished by distributing the retention members 254 substantially around the internal circumference of the tool, and making the retention members 254 relatively bluntly shaped with non-traumatic edges, or by constructing them from an atraumatic material, such as a deformable polymer, to avoid cutting or otherwise damaging the biological unit.

Figure 15A:
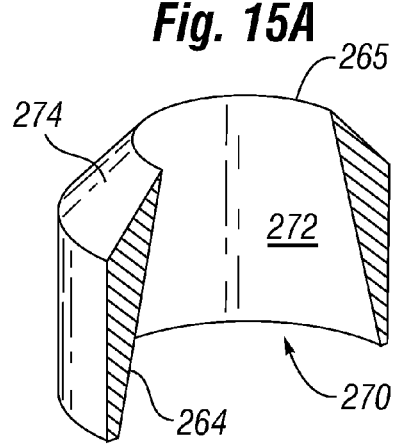
FIGS. 15A and 15B are cutaway perspective views of alternative retention members that could be used, for example, in the tool of FIG. 14A.
Figure 14A:
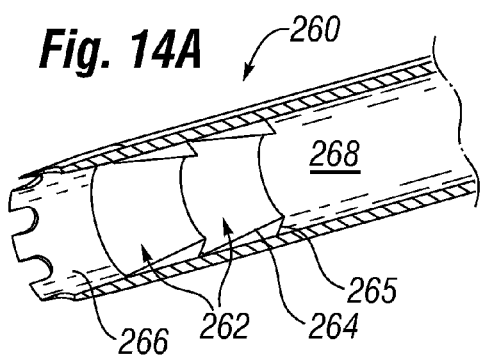
FIG. 14A is a cutaway perspective view of a distal end of a biological unit removal tool of the present invention having axially spaced rows of retention members.
Figure 14B:
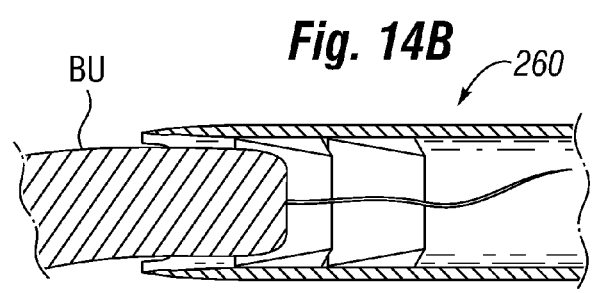
FIG. 14B is a longitudinal sectional view of the removal tool of FIG. 14A shown receiving a biological unit therein.

FIGS. 14A-B illustrate an alternative a biological unit removal tool 260 of the present invention having axially spaced rows of retention members 262. In this embodiment, the retention members 262 extend continuously around the internal circumference of the tool 260 with an unchanging radial cross-section. In a preferred embodiment, the cross-section is a wedge shape having a gradually angled leading edge 264 and a trailing edge 265 as seen in FIG. 15A that may be sharply angled or may be rounded or otherwise configured so as to be atraumatic. Indeed, this is one possible cross-section for the discrete retention members 254 shown in FIG. 13.

There are two exemplary annular retention members 262 shown within the tool 260 located just proximal to a distal tapered region 266. The retention members 262 may be formed directly (e.g., by molding or machining) into an inner wall of the tool 260, but may be inserts that are, for example, bonded to the internal lumenal surface 268. For instance, an insert 270 is shown in partial sectional view in FIG. 15A. The revolution of the relatively shallow taper of the leading-edge 264 provides a conical leading surface 272 through which a biological unit BU, such as shown in FIG. 14B, may easily pass. The revolution of the angled trailing edge 265 defines a conical trailing surface 274 that helps retain the biological unit within the tool 260.

Figure 15B:
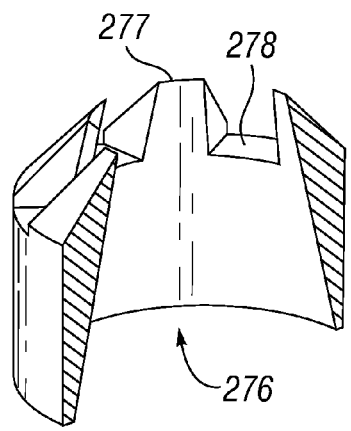

In an alternative embodiment shown in FIG. 15B, a retention member insert 276 shares certain attributes with the insert 270, but includes a discontinuous or interrupted trailing edge having raised segments 277 separated by troughs 278. The trailing edge is shown as crenellated of, like the top edge of a castle, though other discontinuous configurations, such as a more curvilinear design, are also contemplated. Removal of the material to form the troughs 278 present less resistance to passage of a biological unit in a proximal direction into the lumen of a corresponding removal tool. However, the raised segments 277 are distributed substantially around the circumference of the tool, and thus effectively impede distal movement of the biological unit therein. Again, because they are distributed around the circumference of the tool they are more effective in retaining the biological unit therein and less likely to cause damage to the biological unit.

The inserts 270, 276 could be as little as 0.5 mm long in axial dimension and up to 6-7 mm long. In embodiments with retention members, the biological unit is typically removed out of a proximal opening of the tool, since the retention members prevent removal through the distal end opening. In some systems, the biological unit passes directly from the removal tool in the proximal direction into a storage system, or into a tool used to perform further processing. For example, follicular units harvested using the removal tools of the present invention may be transported directly from the removal tool lumen into a receptacle of an implantation cartridge for use in an implant procedure.

FIG. 16 is a cutaway perspective view of an alternative biological unit removal tool 280 that, like the embodiments of FIG. 13-15, includes distal tip structure to prevent transection of biological units, as well as retention members to hold the biological unit within a lumen 282. More particularly, the removal tool 280 includes a crown-shaped distal tip 284 having alternating cutting and relief segments 285, 286. The tool 280 also has a plurality of axially-spaced rows of discrete circumferentially-spaced retention members 287. The retention members 287 resemble those illustrated in FIG. 13, and are shaped as rearwardly-oriented splines or vanes. The retention members 287 may be formed, for example, on two annular adapters; namely, a distal adapter 288 including the distal tip 284, and a proximal adapter 289. Both the distal and proximal adapters 288, 289 may include mating structure as shown, and the proximal adapter 289 may include structure for coupling to a distal end of an elongated body of the tool 280. In one embodiment, the illustrated components are formed of stainless steel, but may also be molded from suitable polymers. With this arrangement, any number of axially-spaced rows of retention members can be added to the distal end of the tool 280. Providing multiple axially-spaced rows of substantially circumferentially distributed retention members further enhances the ability of the tool 282 retain the biological unit in the lumen 282.

FIG. 17 illustrates a further biological unit removal tool 290 of the present invention having a plurality of axially-spaced rows of circumferentially continuous retention members 292. Although shown continuous, each of the retention members 292 may be formed like either insert 270 of FIG. 15A or insert 276 of FIG. 15B, or the retention members may be configured differently from one another. The inserts 292 may be formed of a relatively rigid material, such as stainless steel, or may be formed of a lubricious material such as Teflon, or a softer more deformable material such as silicone so as to be atraumatic to the biological unit within the tool 290.

For instance, FIG. 18 shows yet another embodiment of the biological unit removal tool 300 having an internal retention member 302 made, at least partially, of a lubricious material such as Teflon. Teflon is relatively slippery and the retention member 302 may be formed with rounded corners so that biological unit is not cut or otherwise damaged. The retention member 302 includes a leading-edge taper 303 followed by an inner cylindrical bore 304, both of which exerts a relatively uniform or circumferentially-distributed retention force on the biological unit. The retention member 302 may comprise a tubular insert separate from an elongated body 305 of the tool 300 and held within the tool lumen 306 by an annular lock member 308. For example, a stainless steel ring adhered or otherwise bonded to the lumen 306 may form the lock member 308. Desirably, the retention member 302 is somewhat flexible so as to be positioned within the lock member 308 and permitted to expand so that a mating cavity on the exterior of the retention member receives the lock member. Of course, other means for securing the retention member 302 within the lumen 306 are possible.

FIG. 19 illustrates a still further biological unit removal tool 310 wherein a plurality of elongated discrete circumferentially-spaced retention members 312 extend inward from the tool lumen 314. The longitudinally-oriented retention members 312 provide a more distributed retention force on a biological unit within the tool than discrete retention members described above. Because the retention members 312 are in the form of circumferentially-spaced elongated splines, they also are relatively efficient in transferring torque from the tool 310 to a biological unit therein. During the process of extracting the biological unit, the tool 310 may be rotated to help break bonds between the biological unit and surrounding tissue.

As mentioned above, it may be desirable to provide a retention member within the biological unit removal tool that has one or more features that are atraumatic to the biological unit. For instance, any sharp edges may be rounded, the retention structure may be more evenly distributed around the luminal circumference or axially, or the material may be lubricious, or soft or deformable. It should be understood that any of the embodiments described herein may incorporate one or more of these features. For instance, the discrete retention members 254 of FIG. 13 may be formed of a deformable material, such as silicone, so as to be less damaging to the biological unit. FIGS. 20-22 illustrates three embodiments which utilize deformable material for the retention members.

FIG. 20 illustrates a removal tool 320 having a substantially tubular retention member 322 made of a deformable material, such as silicone. The retention member 322 features a plurality of axially-spaced projections or ribs 324, which in the illustrated embodiment are in the form of a helical screw thread. In the exemplary embodiment, portions of an elongated body 325 are removed leaving connected rings 326 around which the retention member 322 may be molded. Of course, there are other ways to affix the retention member 322 to the removal tool 320. This embodiment combines a number of features previous described, including the atraumatic material, the rearwardly-directed ribs 324, and the helical arrangement of the ribs which enables the tool 320 to be screwed into tissue surrounding a follicular unit after which withdrawal of the tool tears the captured follicular unit from the body tissue.

FIG. 21 is a cutaway perspective view of another biological unit removal tool 330 having an exemplary internal retention member 332 also formed of a deformable material. The retention member 332 may be silicone and molded around a fixed lock member 334 within the lumen of the tool. The tool further incorporates an actuating member 336 for deforming the retention member 332. More specifically, the actuating member 336 may comprise, for example, a solid or hollow rod, or a tubular piston that linearly translates within the tool 330 to alternately compress and release the retention member 332. By axially compressing the retention member 332 it deforms inward and applies a radial force on a biological unit positioned therewithin. The embodiment of FIG. 21 demonstrates that a retention member may be movable between a retention position and a release position.

FIG. 22 illustrates another biological unit removal tool 340 utilizing a movable retention member. More particularly, the retention member comprises a plurality of spaced deformable rings 342 (for example, similar to that described in FIG. 21) that are separated by relatively rigid rings 344, 346. A distal ring 344 features a lead-in taper 345, while two spacer rings 346 are identical and annular. The distal ring 344 is desirably fixed with respect to the tool 340, while the spacer rings 346 are permitted to slide axially within the tool. An actuating member 348, which may be in the form as described in reference to FIG. 21, alternately applies an axial compressive force to an adjacent deformable ring 342. The application of the distal force by the actuating member 348 causes all three (in this example) of the deformable rings 342 to be axially compressed, and thus deform or constrict inwardly. In operation, the tool penetrates a body surface such that a biological unit is positioned within the retention member, then the actuating member 348 is displaced so that the deformable rings 342 clamp onto the biological unit. The deformable rings 342 may be made of any appropriate material, for example, silicone or rubber, alternatively, they could be filled with gels or fluids to be deformable. The fixed ring 344 and spacer rings 346 may be made of relatively rigid material such as stainless steel, Teflon, titanium, or a suitable relatively rigid polymer.

Figure 23A:
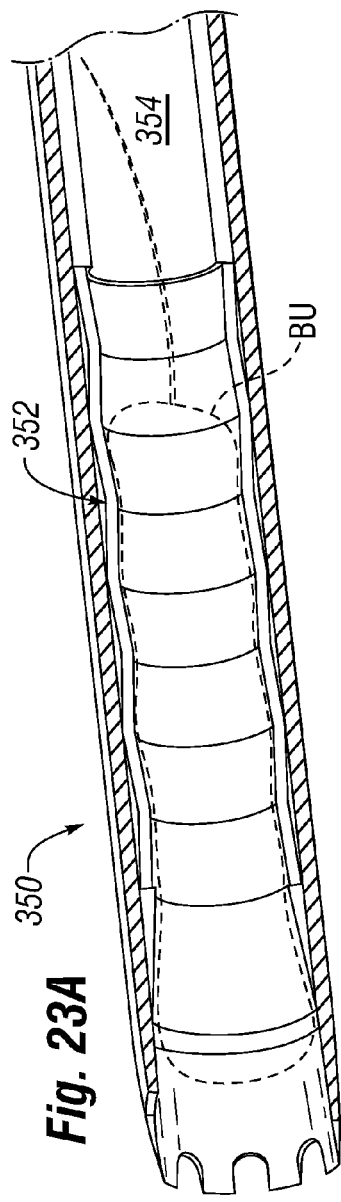
FIGS. 23A and 23B are cutaway perspective views of a biological unit removal tool of the present invention having an accordion-like internal retention member shown, respectively, in its retracted and retention positions.
Figure 23B:
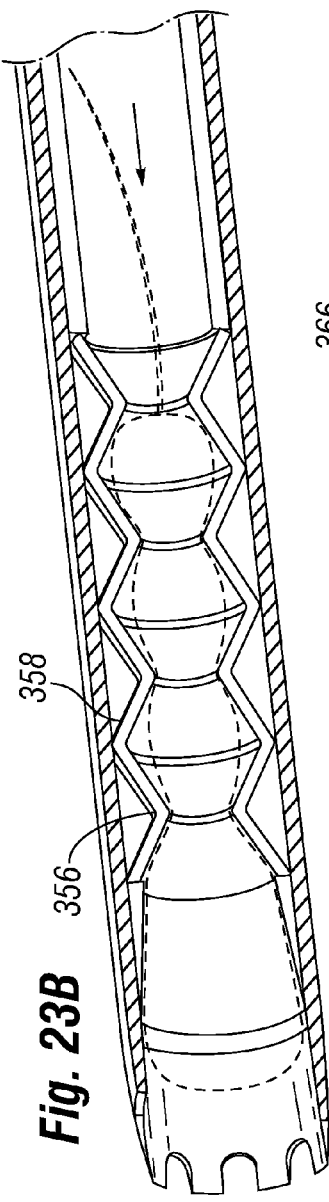

FIGS. 23A and 23B are cutaway perspective views of a biological unit removal tool 350 having an accordion-like internal retention member 352 shown, respectively, in its retracted and retention positions. The tool 350 features an actuating member 354, for example, in the form of a linearly movable tubular rod which acts on a proximal end of the retention member 352. Distal compression of the retention member 352, as seen in FIG. 23B, forms alternating inward creases 356 and outward creases 358 along the retention member. The inward creases 356 contact and constrain a biological unit BU much like axially-spaced circular retainers.

Figure 24:
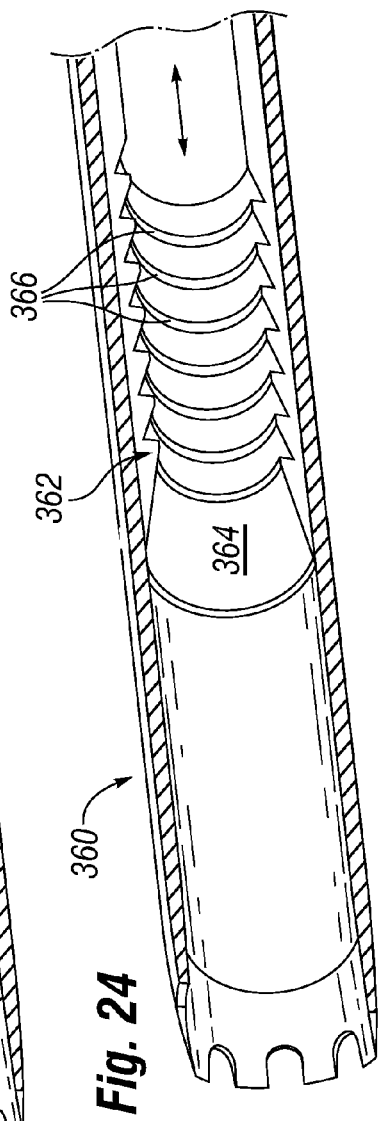
FIG. 24 is a cutaway perspective view of another biological unit removal tool of the present invention having a linearly-movable tubular retention member.

FIG. 24 illustrates still another biological unit removal tool 360 having a linearly-movable tubular retention member 362. The retention member 362 includes a lead-in taper 364 and a series of axially-spaced ribs 366 along a substantial portion of the length thereof. Movement of the retention member 362 permits re-positioning of it closer or further from the distal tip of the tool 360 as needed. The removal tool 360 can surround the biological unit, such as a follicular unit (FU), and then retention member 362 slides around the FU with the guidance of lead-in taper 364. Once the FU enters the retention member 362, then the removal tool 360 along with retention member 362 can be retracted from the body surface together.

FIGS. 25A-25E are alternative biological unit removal tools of the present invention having apertures formed in side walls thereof. One way to retain a biological unit within the tool lumen is to provide openings in the elongated body into which the tissue of the biological unit may expand. At a minimum, one or more openings act like the projecting retention members described above in that they present edges that create frictional contact with the biological unit. Additionally, if the biological unit expands into a side opening then greater torque can be applied to it when trying to sever the final tissue bonds holding it to its surrounding matrix. The descriptions below use the example of follicular unit harvesting, though the reader will understand that the devices more generally may be used to remove biological units from a body surface. Furthermore, various apertures may be combined with any of the other retention features described in the present application to enhance the ability to retain tissue.

Figure 25A:
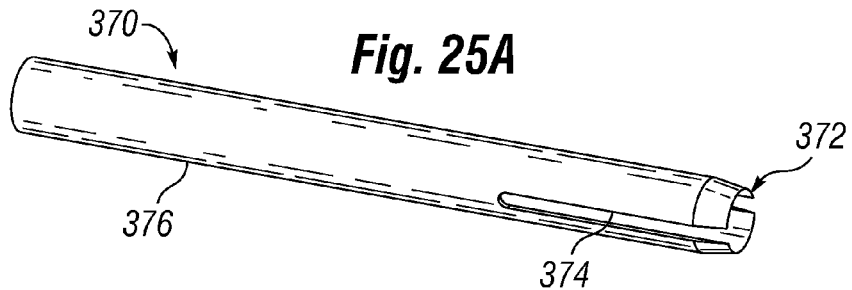
FIGS. 25A-25E are alternative biological unit removal tools of the present invention having apertures formed in a side wall thereof.

In the embodiment of FIG. 25A, a hair follicular unit harvesting cannula 370 has an inwardly tapering, sharpened distal tip 372, and a plurality of circumferentially spaced, axially aligned slots 374 cut into a side wall 376 of the cannula 370. Desirably, there are two diametrically-opposed slots 374. As with the windows 414 of cannula 410 in FIG. 25E, below, the slots 374 will engage (or "grab") the tissue of a cannulated follicular unit to help retain the follicular unit within the lumen of the cannula 370 as it is twisted (to separate the bottom portion of the follicular unit from the tissue bed) and withdrawn from the respective body surface.

Figure 25B:
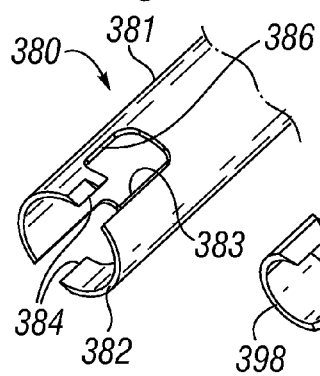

FIG. 25B depicts still another embodiment of a harvesting cannula 380 having an elongated tubular body 381 having a lumen sized to receive a biological unit and a distal end 382 configured to penetrate a body surface. A pair of axially-aligned slots 383 open to the lumen on opposing sides of the cannula body, offset approximately 180° about the outer circumference. Axially-oriented side-cutting edges 384 are provided along an axial edge of each slot 383. Again, the leading (or distal) facing edge 382 is flat or blunted for forward movement through tissue, with the respective cutting edges 384 providing a sharpened initial cut into the skin when being rotated about the tool axis.

The slots 383 each have widened portions 386 located proximally of their respective side-cutting edges 384 so that, after the cannula 380 has been advanced through the skin (e.g., while being rotated about its axis) and subcutaneous tissue surrounding a respective follicular unit (e.g., by using blunt tissue dissection), the cannula may then be rotated an additional (approximately) 15°, and more generally in a range of 5-30°, so that the widened slot portions 386 will "lock" into a zone of expanding subcutaneous tissue to help extract (i.e., by engaging or "grabbing" the tissue) the follicular unit as the cannula 380 is withdrawn. This design provides a relatively "blunted" distal end as the cannula 380 is moved in a forward-plunging motion, with the cutting motion only applied circumferentially, and not axially, for initial skin penetration. As with the above-described harvesting cannula embodiments, the cannula 380 (as well as additional harvesting cannulas described below) may be manufactured from stainless steel hypodermic tubing, with the slots 383 and cutting edges 384 made in accordance with well-known manufacturing techniques.

Figure 25C:
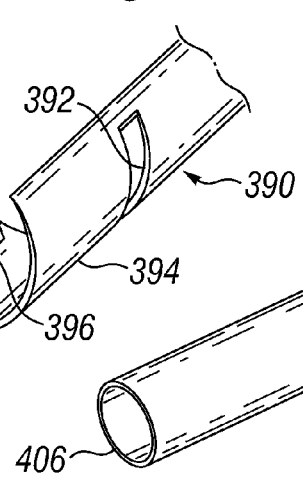

FIG. 25C depicts still another embodiment of a harvesting cannula 390, in which a single (or double in one variation) helix slot 392 is cut out of the cannula wall 394. The helix slot 392 captures a zone of tissue around a follicular unit as the cannula 390 is rotated and advanced into the skin and subcutaneous fatty layer at the pitch of the helix (i.e., in a corkscrew fashion). An axially-oriented side-cutting edge 396 is provided along the distal portion of the helix slot 392, which cuts through the skin as the cannula 390 is rotated about its axis. As with the above-embodiments, it may be preferable to stop rotation of the cannula 390 after initial skin penetration, and rely on blunt tissue dissection as the cannula is moved further into the tissue. Again, using a side cutting element 396 results in a more blunted distal end 398 when the cannula 112 is being moved in a forward-plunging motion through the skin and subcutaneous tissue, since the cutting element is aligned and moved circumferentially and not axially.

Figure 25D:
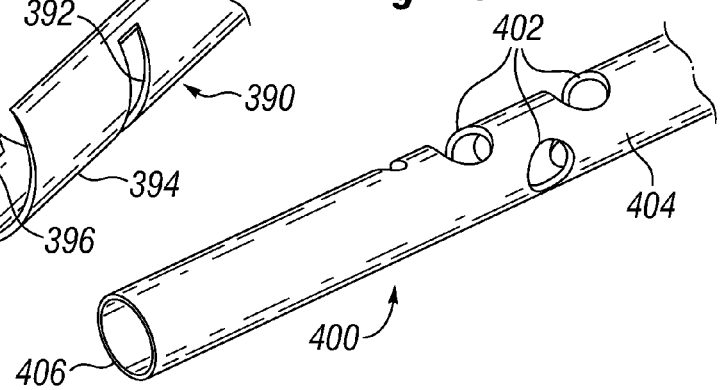

FIG. 25D depicts yet another embodiment of a harvesting cannula 400, this one having a number of side holes 402 cut out of the cannula body 404 at a distance set back from the distal end cannula opening 406, so that the holes 402 will capture top layers (epidermis and dermis) of the skin surrounding the follicular unit as they (the skin layers) expand after being cut, thereby helping to retain and hold hair follicle(s) extending out of the follicular unit as the cannula 400 is retracted. It will be appreciated by those skilled in the art that the side holes 402 may be suitable for use in any of the foregoing harvesting cannula embodiments.

Figure 25E:
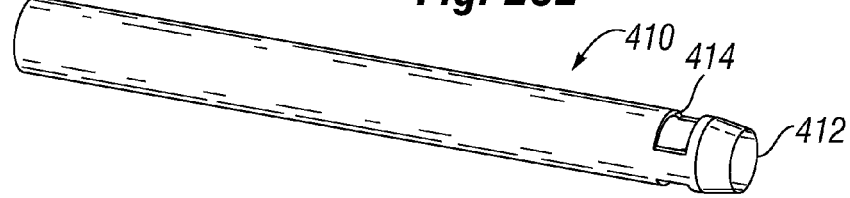

FIG. 25E illustrates yet another embodiment of a hair follicular unit harvesting cannula 410 having an inwardly tapering, sharpened distal tip 412, and a pair of circumferentially spaced windows 414 cut into a side wall 406 of the cannula 410. As discussed with respect to previous embodiments, the windows 414 will engage (or "grab") the tissue of a cannulated follicular unit to help retain the follicular unit within the lumen of the cannula 410 as it is twisted (to separate the bottom portion of the follicular unit from the tissue bed) and withdrawn from the respective body surface.

Figure 26A:
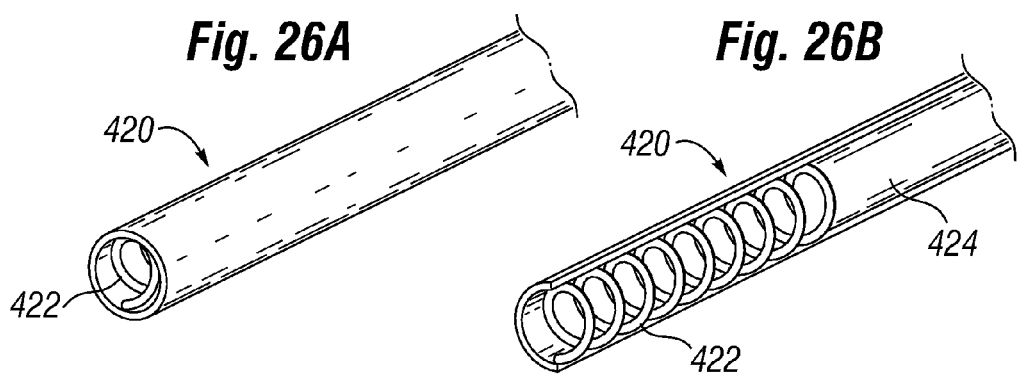
FIGS. 26A and 26B are perspective and cutaway views of a still further exemplary biological unit removal tool of present invention having an internal retention member in the form of a coil spring.
Figure 26B:
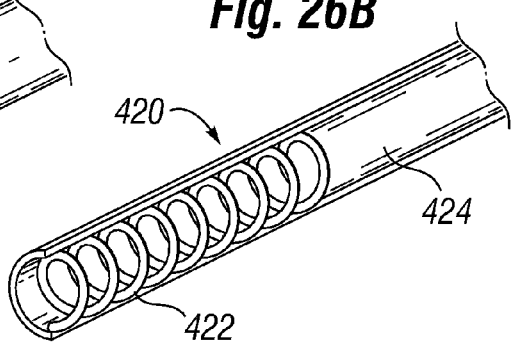

FIGS. 26A and 26B depict still another embodiment of a removal tool 420 having an internal retention member in the form of a helical coil spring 422 disposed along the wall of its inner lumen 424. As the cannula 420 is rotatably advanced through the skin and into the subcutaneous tissue, the spring engages (wraps around) a track of the follicular unit tissue (in a similar manner as the helix slot 392 in cannula 390 of FIG. 25C) to aid in extraction of the follicular unit from the body tissue. It will be appreciated that, instead of the spring 422, "rifling" features, such as a spiral ridge or groove (or portions thereof), may be incorporated into the inner lumen wall to physically engage the follicular unit. It will further be appreciated by those skilled in the art that the use of the spring 422 or suitable rifling feature carried or incorporated in the wall of the inner cannula lumen 424 may be used in any of the foregoing described harvesting cannula embodiments for engaging and securing the follicular unit being harvested.

FIG. 27 is a cutaway perspective view of a biological unit removal tool 430 having a combination of features described herein. In particular, the tool 430 has an elongated body 432 defining a crown-shaped distal tip 433 leading to an internal lumen 434. A leading tapered insert 435 and a trailing tapered insert 436 sandwich therebetween a spring-like retention member 438. The tapered inserts 435, 436 help reduce sharp corners and thus trauma to a biological unit captured within the tool 430.

FIGS. 28A-28D are perspective, elevational, and sectional views of a still further biological unit removal tool 440 featuring a series of circumferentially-spaced internal retention dimples 442 located just proximal from a distal tip 444. Each dimple 442 includes a concave depression leading to a small aperture 446. The inward projection of the dimples 442 helps retain a biological unit within the tool 440, while the apertures 446 may help grab the tissue to facilitate the application of torque thereto. Three dimples 442 are shown at the same axial location, though more than three in axial rows, for instance, may be provided.

FIGS. 29A and 29B illustrate two stages in an exemplary process for forming an internal retention member of the present invention. An indent or dimple 450, much like the dimples 442 described above, is formed in a sidewall 452 of an elongated body. The dimple 450 may be formed with various implements, including a punch or other such device for stainless steel, or with a mold for polymer. A proximal portion of the dimple 450 is then removed, as seen in FIG. 25B, such as with machining or laser cutting. The resulting projection 454 extends into the tool lumen in a proximal direction and is effective in permitting passage of a biological unit while retaining it within the lumen.

FIGS. 30A-30C depict a further alternative exemplary follicular unit harvesting cannula 460 having a beveled distal tip 462. A portion of the cannula 460 is cut axially inward from the distal tip 462 (e.g., using a laser) to create a bendable "finger" 463 having a width of approximately 20-40% of the total circumference of the cannula 460. The remaining distal portion 464 of the cannula 460 forms a trough into which the distal end 466 of the finger portion 463 may be bent, e.g., using a telescoping outer cannula 467 or other mechanical means. A harvested follicular unit (not shown) may therefore be captured in the trough by the finger portion 463 after the distal tip 462 has punctured the skin and the distal portions 463 and 464 are pushed through the skin layers and into the subcutaneous tissue to a desired depth surrounding the hair follicular unit.

As mentioned above, a movable retention member may advantageously be incorporated into a biological unit removal tool in accordance with the present invention. A number of configurations of movable retention members are shown in FIG. 31-33. As in the previously described embodiments, the removal tools typically include an elongated body having a lumen sized to receive a biological specimen or unit, and a distal tip configured to penetrate a body surface. Once the biological unit has been received in the lumen, a retention member moves from a retracted position to a retention position. In order to impede distal movement of the biological unit, the retention member physically blocks or radially contacts (e.g. clamps) the biological unit. The retention member can be incorporated into the elongated body or extend into the lumen from outside the elongated body. In all of these configurations, the retention member moves into a position which prevents the biological unit from exiting the lumen.

FIGS. 31A-31D illustrate an exemplary biological unit removal tool 470 having a spring-loaded retention finger 472. In this illustration, the tool 470 includes an elongated body 474 held within a tool holder or collet 476. The collet 476 forms a part of a larger mechanism that may be manually manipulated or may be part of a robotic system. In the illustrated embodiment, the elongated body 474 has a distal tip 478 opening to an internal lumen 480 that is in fluid communication with a plenum 482 within the collet 476. The removal tool 470 is connected to a source of reduced pressure so that a negative pressure differential created in a proximal direction through the lumen 480 facilitates extraction of a biological unit from a tissue bed, and further may be used to transfer the biological unit through the elongated body 474 and into a storage cartridge or other storage means. As will be understood by those skilled in the art, a negative pressure differential, such as vacuum, may be implemented with other shown and described embodiments of the present invention to facilitate extraction of a biological unit.

As seen in the detailed views of FIGS. 31C and 31D, the retention finger 472 includes a hook 484 at the distal end thereof that projects radially through an aperture (not numbered) in the sidewall of the elongated body 474. The hook 484 has an end that is angled so as to form a lead-in ramp and a distal tip 486. Because it is spring-loaded, passage of a biological unit into the lumen 480 displaces the hook 484 outward into a retracted position, after which it is biased inward again into the retention position shown. If the biological unit has passed the hook 484, the physical presence of the hook helps prevent it from exiting the distal tip 478. Alternatively, the hook 484 may radially contact or even embed itself within a side of the biological unit to retain it within the lumen 480. The shape of the hook 484 with the distal tip 486 permits proximal movement of the biological unit but prevents distal movement.

Figure 32A:
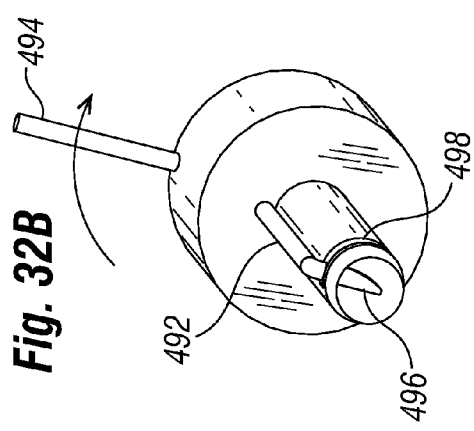
FIGS. 32A and 32B are perspective views of a biological unit removal tool of the present invention having an exemplary rotatable retention finger.
Figure 32B:
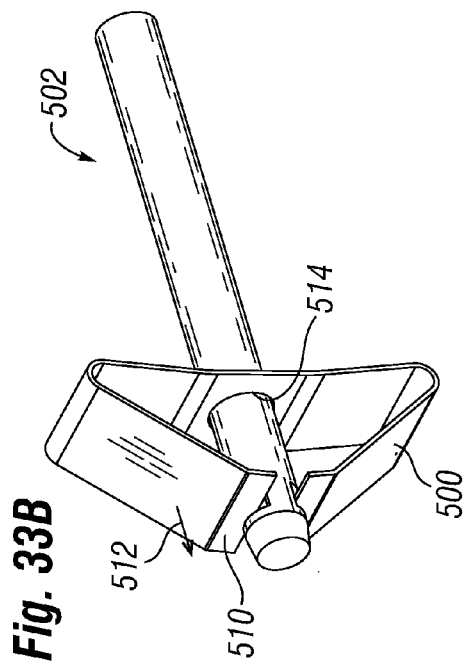

FIGS. 32A and 32B illustrate another biological unit removal tool 490 having a rotatable retention finger 492. Rather than being spring-loaded, as in the previous embodiment, the finger 492 is selectively rotated, such as by actuation of a lever 494, to cause a distal hook-type end 496 of the rotatable retention finger 492 to enter into the lumen of the tool 490 through a side slot 498. The lever 494 may be actuated manually, connected to an electronically-controlled actuation mechanism, or may be automatically controlled within a robotic system. In any of these possible configurations, radially inward movement of the end 496 of the retention finger 492 into the tool is timed to prevent distal movement of a biological unit therein.

Figure 33A:
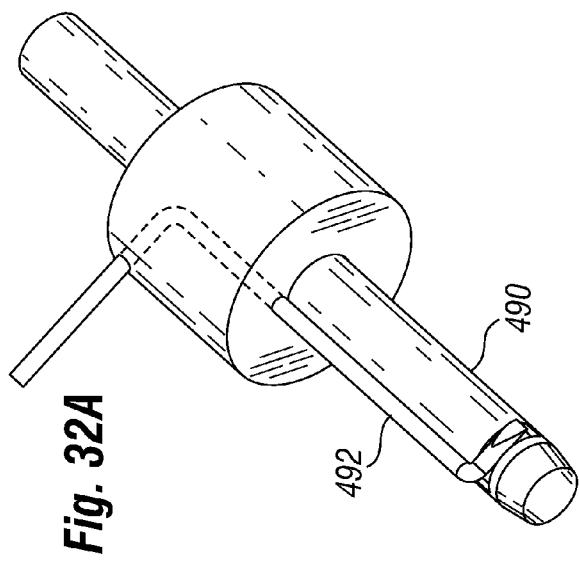
FIGS. 33A and 33B are perspective views of a biological unit removal tool of the present invention having an exemplary movable retention clip on an exterior thereof and shown, respectively, in retracted and retention positions.
Figure 33B:
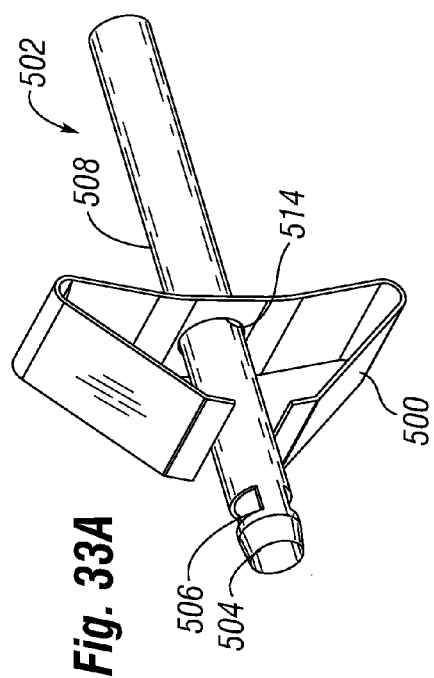

A further movable retention member is illustrated in FIGS. 33A and 33B. Specifically, a movable retention clip 500 translates axially on an exterior of a removal tool or cannula 502 between retracted and retention positions. The exemplary cannula 502 features an inwardly tapering distal tip 504, and two circumferentially spaced windows 506 cut into a side wall of an elongated body 508. As with the windows 414 of cannula 410 in FIG. 25E, the windows 506 will engage (or "grab") the tissue of a cannulated follicular unit to help retain the follicular unit within the lumen of the cannula 508 as it is withdrawn from the respective body surface.

Additionally, the clip 500 slides axially on the cannula body 508 between a retracted position in FIG. 33A and a retention position in FIG. 33B. The exemplary clip 500 has two inwardly biased teeth 510. Once a biological unit such as a follicular unit is cannulated within the inner lumen of the cannula 502, and the cannula is partially withdrawn from the respective body surface to reveal the windows 506, the clip 500 slides distally down the cannula body 508 (indicated by arrow 512 in FIG. 33B) along a guide hole 514 in the proximal end of the clip 500, until the inwardly biased teeth 510 engage and compress (to thereby further secure) the tissue through the windows 506, as the cannula 502 is completely withdrawn from the body surface. Although not shown, axial movement of the clip 500 may be accomplished through a stepper motor, pneumatic piston, or other such mechanism.

Concentric Tube Biological Unit Removal Tools

In the previously described embodiments of the present invention various features for improving retention, reducing a flap and transection rates were shown incorporated in a single elongated body that is used to penetrate tissue and remove the biological unit. The described features enable a removal tool to be sharp to cut through the epidermis and dermis, and at the same time dull to pass through fatty tissue that surrounds a biological unit such as a follicular unit. Another approach in solving the problems associated with the prior art device is to separate the functions of the removal tool into two different tubes that are utilized in concert. A number of dual-needle or concentric tube embodiments are described below, but it should be understood that any of the tools and specific features described above may be combined with a second tool in a similar manner, unless there is some mutually exclusivity between the tools.

In a first concentric tube embodiment, FIGS. 34A-C depict the distal end portion of an alternate embodiment of a tool assembly 520 for harvesting biological units 522 from a body surface 524. The tool assembly 520 includes a pair of coaxially disposed cannulas 526 and 528 that are moveable relative to one another. In particular, a collet 530 holds (and moves) an outer cannula 526 having a blunt distal end opening 532 into the skin surface 524. As the blunt distal end 532 of the outer cannula 526 is moved axially against (thus stretching and tightening, but not penetrating) the skin surface 524, an inner cannula 528 having a sharpened distal end 534 is thrust at high speed through the inner lumen of the outer cannula 526 to pierce the skin surface 524 to a depth of approximately 1 to 2 mm. This allows the outer cannula 528 to continue its progress (i.e., without stopping its relative movement) through the skin surface 524 and into the cutaneous and subcutaneous tissue to a dept of approximately 5-7 mm using blunt dissection (seen in FIG. 34C), to completely capture, for example, the follicular unit 522. Both cannulas 526 and 528 are then withdrawn together from the skin surface 524.

In the concentric tube embodiment of FIGS. 34A and 34B, therefore, the removal tool has two concentric needles or tubes. An inside needle is sharp or semi-sharp, such as with the exemplary distal tip 72 of the tool of FIG. 5A, and an outside needle is relatively dull or less able to cut through tissue than the inside needle. The outside needle moves slowly down around the inner needle, whereas the inside needle makes a sudden and rapid punching motion to form a 0.5-2.0 mm deep circular incision. The outside needle can then follow the inside needle into the circular cut made by the inside needle and continue through deeper fatty tissue to a depth of 5-8 mm. The relatively dull edge of the outside needle will guide any hair follicles into both the inner and outer needles instead of transecting them.

An exemplary embodiment implemented with respect to the embodiment of FIGS. 34A-34C may include a rod or piston 540 connected to a proximal end of the outer tube 526 and movable within a plenum chamber 542. Alternating positive and negative pressure within the plenum chamber 542 therefore advances and retracts, respectively, the outer tube 526. The inner tube 528 may be similarly actuated, or may be connected to a mechanical stepper motor or the like (not shown).

FIG. 34A shows the outer tube 526 disposed above the skin surface 524 and positioned over the hair of a follicular unit 522. The inner tube 528 is then advanced rapidly within the outer tube 526 such that the sharp distal end 534 incises a circular cut in the skin surface 524. Subsequently, the outer tube 526 follows over the inner tube 528 and continues deeper below the skin surface 524 to surround the follicular unit 522. At this point, retention means (such as various retention members described above) within the inner or outer tubes may take effect or be actuated, and the assembly pulled free of the skin surface 524 such that the follicular unit 522 is captured therein. Depending on the specific design and application, and depending on the desirable precise order of withdrawal of the inner and outer cannulas from the skin, the retention member may be incorporated into the inner, or outer cannulas, or both. Suction within a lumen 544 of the inner tube 528 may be used to further transfer the follicular unit 522 in a proximal direction.

The concentric tube embodiment described above relies on the formation of a circular incision made by the sharp inner tube after which the less sharp outer tube follows into the tissue. One undesirable possibility is the enlargement or destruction of the clean circular incision by the blunt outer tube. To help prevent such damage, the outer tube may be rotated while the descending into the incision to reduce the chance of catching on the incision from direct linear movement. Alternatively, a small annular space between the inner and outer tubes may be designed so that the outer tube rotates slightly off the axis of the inner tube so as to wobble or be mis-aligned with respect thereto. For that matter, both tubes might be caused to rotate off-center from their own axes and wobble. The wobbling from one or both tubes may allow the outside tube to spiral into the opening created by the inside tube. The removal tool and corresponding process described with reference to FIGS. 34A-C may be substantially automated, and it is especially fitted for use with robotic or computer-controlled systems.

Another solution for this potential problem with concentric tubes is to supply an axial projection on the outer tube which acts something like a shoehorn in helping the outer tube follow the inner tube through the circular incision. FIGS. 35A-35B and 36A-36C illustrate one example of such an apparatus for a biological unit removal tool 550 of the present invention. The tool 550 includes an inner tube 552 that slides axially within a lumen of an outer tube 554. The outer tube 554 has a distal tip 556 defining a generally circular periphery and a lip portion 558 that extends farther than the remainder of the periphery. In particular, the lip portion 558 resembles a small projection that is tapered to provide a streamlined profile against the inner tube 552, as seen in the cross-section of FIG. 35B. The axially extending lip portion 558 easily passes into a circular incision created by the leading inner tube 552, especially if the outer tube 554 rotates.

It is often beneficial to irrigate surgical fields, such as during the removal of biological units, namely multiple follicular units. The present invention is particularly useful in the context of robotic hair transplantation in which an automated system may be used to harvest multiple follicular units from a body surface, including from the strips of explanted skin containing follicular units. Because of the speed at which such a system works, constant irrigation with, for example, saline will help increase the yield by providing cooling and lubricious fluid at the distal end of the removal tool, it will also help to keep the harvested follicular units moist.

One exemplary embodiment for delivering a fluid or gas, for example, saline is seen in FIGS. 37A and 37B. A concentric tube biological unit removal tool 560 mounts at the distal end of a holding mechanism 562. A saline inlet tube 564 opens into a concentric space 566 (see FIG. 37B) between an inner tube 568 and outer tube 570. The space 566 leads to a plurality of distal ports 572 near the distal tip of the inner tube 568. Introduction of pressurized saline (or other appropriate fluid or gas) through the ports 572 facilitate passage of a biological unit or follicular unit into and through a lumen 574 of the inner tube 568. Moreover, the application saline to the biological unit just after it has been removed from the body is beneficial to prevent its dehydration.

FIG. 38 is a perspective view of the distal end of an outer tube 580 that may be used in a modified version of the system of FIG. 37A. Tube 580 may include a circular recessed region 582 that opens to longitudinal channels 584. Any desired number of the longitudinal channels may be used. The channels continue axially through a side wall of the tube 580 and each open at a delivery port 586 at a distal tip 588. This configuration shown in reference to concentric tube embodiments can be modified to provide fluid or gas delivery in the single tube embodiments of the present invention.

Regardless of whether it is used in a single tube implementation or in "needle-in-needle" implementation of the present invention, a plurality of distal ports 586 could be used to deliver certain gas or fluid under pressure to the distal end of the removal tool to assist in separating or tearing a biological unit from the connective tissue that holds and pulls back such biological unit (e.g. follicular unit) from the removal tool. In the embodiments of the method of present invention where the removal tool is rotated inside the skin to facilitate the removal of the biological unit, delivery of the fluids or gasses under pressure to the distal end may create additional force right below the end of the removal tool to assist in separating the biological unit caught in the distal end of the removal tool from the connective tissue. In a preferred configuration, there are between 1-10 of the distal delivery ports (such as ports 586 in FIG. 38) each with a diameter of between 0.005-0.020 inches (0.127-0.508 mm). Various suitable medical fluids or gasses may be used including saline, $N_2$ or $CO_2$. A chemical fixative solution may even be used to treat the biological units immediately upon extraction. Pressures between 0.1 and 10.0 psi are believed preferable.

FIGS. 39A-39E are various views of an exemplary biological unit removal tool 590 that incorporates separate conduits 592 defining lumens or channels for providing fluid or gas flow to the distal end thereof. In contrast to the embodiment of FIG. 38, the conduits 592 include ports 594 that open radially inwardly close to a distal tip 596 of the tool. Separate conduits 592 that mate with similarly-shaped slots 598 are somewhat easier to manufacture than the built-in channels and ports in the embodiment of FIG. 38. The exemplary embodiment of FIGS. 39A-39E may be used in a similar manner as described in reference to FIG. 38.

FIGS. 40A-40C depict an alternative follicular unit harvesting tool assembly 600, which includes a tissue piercing cannula 602 having a sharpened (e.g., inwardly tapered) distal end opening 604. As shown in FIG. 40A, the tissue piercing cannula 602 may be advanced forward (indicated by arrow 606), while simultaneously being rotated about its axis (indicated by arrow 608), into a patient's skin and subcutaneous tissue to a depth of approximately 2-3 mm deep surrounding a follicular unit to be harvested. A grasper 610 is coaxially disposed in (and movable relative to) the tissue piercing cannula 602. As shown in FIG. 40B, once the tissue piercing cannula 602 is advanced into the tissue surrounding the selected follicular unit, the grasper 610 is advanced out of (and relative to) the cannula opening 604 (indicated by arrow 612), so that circumferentially spaced fingers 614 of the grasper 610 envelop the follicular unit. The grasper fingers 614 are preferably resilient and have relatively blunt distal ends 615, and reach a depth in the tissue surrounding the follicular unit. As shown in FIG. 40C, once the grasper fingers have enveloped the follicular unit, the cannula 602 is then advanced over (and relative to) the grasper 610 (indicated by arrow 616), to force the grasper fingers to close and firmly engage the follicular unit tissue. Thereafter, the tool assembly 600 is withdrawn from the patient, with the follicular unit being extracted and retained within the grasper fingers 614.

Figure 41:
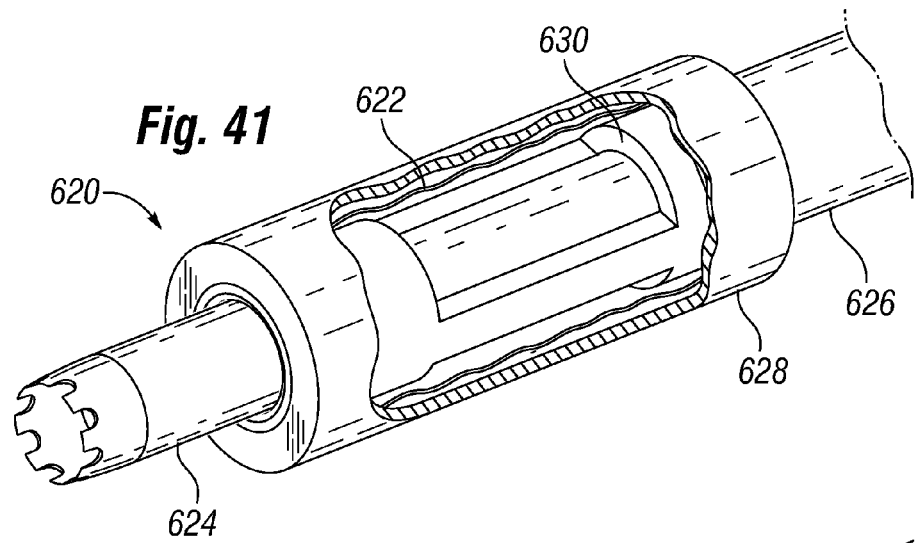
FIG. 41 is a cutaway perspective view of a biological unit removal tool of the present invention having radially constricting member for retaining a biological unit therein.

FIG. 41 is a cutaway perspective view of a biological unit removal tool 620 having radially constricting member 622 therein for retaining a biological unit. The tool 620 has concentric inner 624 and outer 626 tubes, and a cylinder housing 628 mounted around the distal end of the outer tube. As seen in the cutaway portion, the outer tube 626 features one or more elongated windows 630, in this case two diametrically opposed windows. The radially constricting member 622 may take a variety of forms, but in the illustrated embodiment is a flexible membrane (for example, a balloon). Fluid or gas introduced from the outside of the flexible membrane 622 and within housing 628 causes the membrane to constrict inward through the windows 630. In a preferred sequence, a biological unit is received within the outer tube 626 at the location of the windows 630. Inflation of the membrane 622 causes it to constrict (or expand) inward through the window 630, thus applying a radial retention force to the biological unit.

Figure 42A:
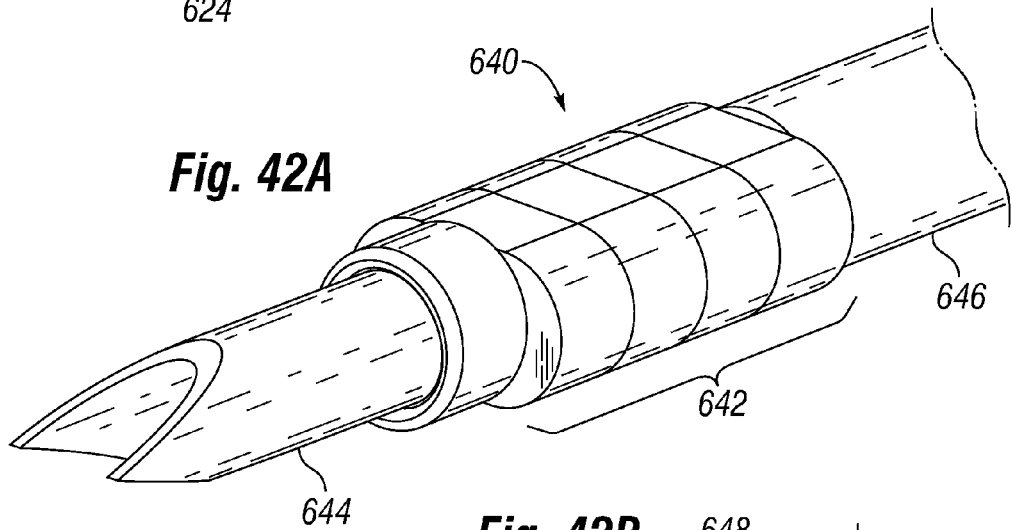
FIGS. 42A and 42B are perspective views of an alternative biological unit removal tool of the present invention having a series of resilient bands for retaining a biological unit therein.
Figure 42B:
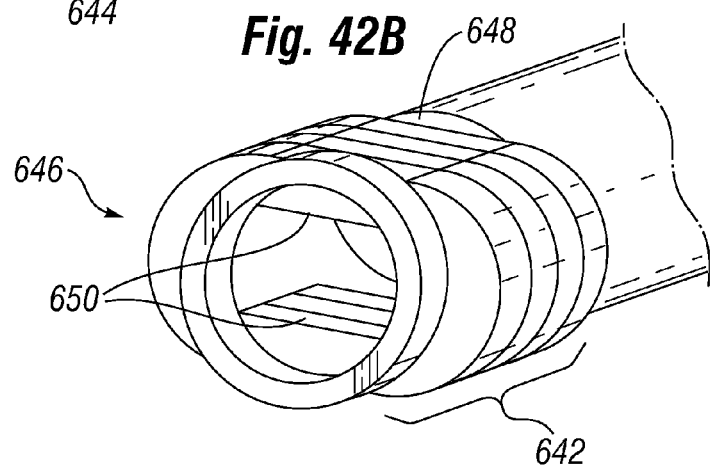

FIGS. 42A and 42B are perspective views of an alternative biological unit removal tool 640 having a series of resilient bands 642 for retaining a biological unit therein. The tool 640 includes an inner tube 644 that slides with an outer tube 646. The distal end of the outer tube 646 is shown in FIG. 42B and includes a pair of diametrically opposed windows 648 that accommodate the resilient bands 642. Inner surfaces 650 of the bands 642 extend inward into the lumen of the outer tube 646 through the windows 648. This projection into the lumen and the resiliency of the bands 642 provides an inward clamping force on a biological unit within the lumen. As seen, the distal end of the inner tube 644 has a configuration similar to that shown in FIGS. 7A-7C, however, any other appropriate disclosed embodiment of the distal tip of the present invention may be substituted therein.

Figure 43A:
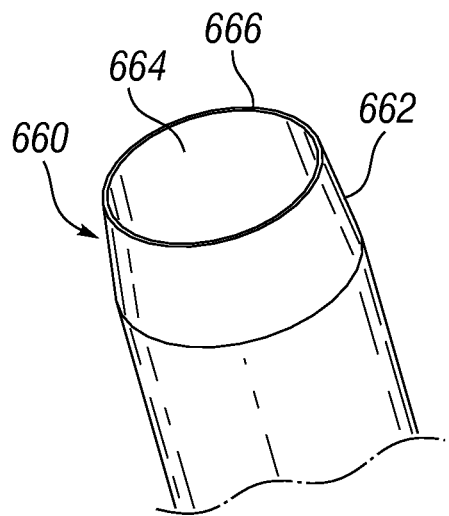
FIG. 43A-43C are perspective views of the exemplary distal ends of several alternative biological unit removal tools for use with the concentric tube embodiments of the removal tool.
Figure 43B:
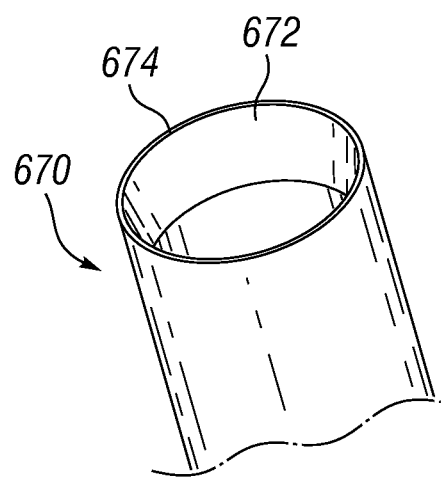
Figure 43C:
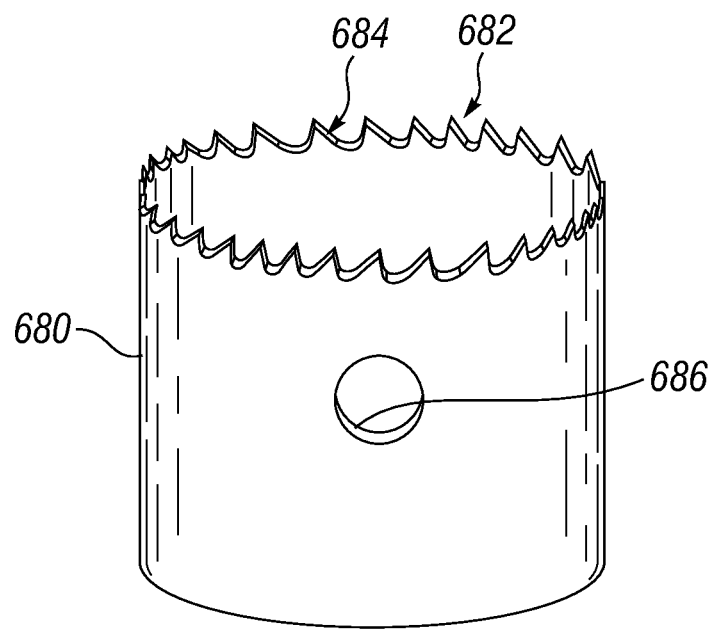

The following FIGS. 43A-43C show different configuration of the distal tip that could be used with either inner or outer cannulas of the concentric tube embodiments of the removal tool. These figures are described in reference to exemplary hair harvesting tool, however, again as with any other disclosed embodiments, the present invention is generally intended to cover tools for removal of various biologic units. FIG. 43A depicts a harvesting cannula 660 having a beveled (or tapered) tip 662 cut to slope (moving in a distal direction) from the outside in, i.e., with the distal end portion of the inner cannula lumen wall 664 having a uniform inside diameter for receiving and retaining the follicular units. The resulting distal end 666 is relatively thin and provides less resistance than would a non-beveled tip when initially penetrating the skin, thereby making a cleaner cut into the skin surface, with less injury to the surrounding tissue, during introduction of the cannula 660. The harvesting cannula 660 may be manufactured, by way of example, from stainless steel hypodermic tubing (e.g., 304 SST, 16.5 Gage) in accordance with well-known manufacturing techniques, and in a similar manner as cannula 140 described above with respect to FIG. 8A.

As mentioned previously, a sharper distal facing (or "leading") edge on the cannula 660 will more easily pierce the epidermal without causing collateral damage, but a duller leading edge will reduce the chance of cutting (dissecting) the portion of the hair follicle lying beneath the skin surface in the epidermal, dermal, and subcutaneous fatty tissue layers. Thus, potential design choices may incorporate aspects of both sharp initial skin penetration, and dull sub-cutaneous (below the skin surface) tissue dissection.

FIG. 43B depicts another embodiment of a harvesting cannula 670, which has an internally beveled tip 672 cut to slope from the inside out, i.e., with the distal portion of the inner cannula lumen wall sloping inwardly in a proximal direction from the distal cannula opening (akin to a very gradually sloped funnel) to thereby reduce the diameter and (slightly) compress, which may improve the frictional retention of, harvested follicular units (i.e., tissue embedding one or more hair follicles) captured within the cannula lumen as it moves through the cutaneous and subcutaneous tissue. As with the outside-beveled tip 662 of cannula 660, the resulting distal end 674 of the inside-beveled tip 672 is relatively thin and provides less resistance than would a non-beveled tip when initially penetrating the skin, thereby making a cleaner cut into the skin surface, with less injury to the surrounding tissue, during introduction of the cannula 670.

FIG. 43C depicts another harvesting cannula 680, this one having a saw-tooth distal end 682, including serrated teeth 684 oriented such that clockwise rotation of the cannula 680 about its axis will cause the teeth 684 to cut into skin and tissue as the cannula is moved axially forward, whereas counterclockwise rotation will cause the teeth 684 to bluntly dissect the tissue. Axially-aligned slots or circular apertures 686 (offset, for example, approximately 180° about the outer circumference when two slots are used) may be cut out of the sides of the cannula 680 to allow the subcutaneous tissue to expand (i.e., after the cutting rotation stops) and be captured and retained in the inner cannula lumen as the cannula 680 is withdrawn. It will be appreciated by those skilled in the art that the tissue-engaging, or "retention" slots or apertures 686 are suitable for use in any of the foregoing and forthcoming harvesting cannula embodiments, and are not at all limited to use with the "sawtooth" embodiment 680 of FIG. 43C.

FIGS. 44A-C depict a further alternative follicular unit harvesting tool 690 in which relative positions of the relatively sharper and relatively duller cannulas are reversed. An outer (tissue piercing) cannula 691 has a sharpened (e.g., outer-beveled) distal end 692 that is coaxially aligned with, and moveable relative to, an inner (duller) cannula 693. The outer cannula 691 is used to initially penetrate the skin surface surrounding a targeted follicular unit. The inner cannula 693 has a dull distal end 694 (best seen in FIG. 44C) and is used for cannulating and retaining a tissue plug including the targeted follicular unit by blunt tissue dissection once the skin is initially pierced by the outer cannula 691.

Furthermore, the outer cannula 691 may have an axially aligned slot 695 through which a radially extending guide pin 696 extends from the outer wall of the inner cannula 693. The inner cannula 693 carries a spring member 697 around (and anchored to) its outer wall, which applies a moderate axial force (in a distal direction) against the proximal end of the outer cannula 691. Notably, the compliance of the spring 697 is preferably much less than that of a patient's skin tissue, so that the spring 697 will compress (and the outer cannula 691 will move in a proximal direction relative to the inner cannula 693) as the outer cannula 691 is pressed against the skin surface. However, the spring 697 will apply sufficient force to normally bias the outer cannula 691 distally relative to the inner cannula 693, as shown in FIG. 44A with the pin 696 in a most proximal position in slot 695, absent a proximally directed counter force made against the outer cannula 691, e.g., by the skin tissue. The entire tool 690 may be optionally rotated (indicated by arrow 699) by rotating the inner cannula 693, which applies rotational torque to the outer cannula 691 via the pin 696.

In use, the tool 690 (as shown in FIG. 44A) is moved distally while (optionally) being rotated, until the sharpened distal end 692 of the outer cannula pierces the skin surface to an initial depth of 2-3 mm into the top skin layer. The counterforce of the skin and underlying body tissue pushes back proximally on the outer cannula 691, causing it to move proximally relative to the inner cannula 693, until the pin 696 reaches the most distal position in the slot 695 (as shown in FIG. 44B), with the blunt distal end 694 of the inner cannula 693 extending through the open distal end 692 of the outer cannula 691 further into the body tissue (e.g., 7-9 mm deep, through the skin surface and subcutaneous fatty tissue) to surround the targeted follicular unit. Thereafter, the tool 690, including the harvested tissue plug containing the targeted follicular unit, is removed from the body surface. Towards this end, the inner lumen wall of the inner cannula 693 may be provided with grooves or some other tissue retention means, as described above. FIG. 44C is an enlarged view of the distal end of the tool 690, showing the distal blunt edge 694 of the inner harvesting cannula 693 extending out of the beveled end 692 of the outer cannula 691.

While various embodiments of the present invention may be used in the manual hand-held removal tools, they could also be beneficially incorporated into automated, or semi-automated systems and devices. Specifically, they could be implemented in the robotically-assisted systems and devices, for example, by being connected to the moveable robotic arm. Some exemplary embodiments of such automated systems are described below in reference to FIGS. 45-46.

Figure 45:
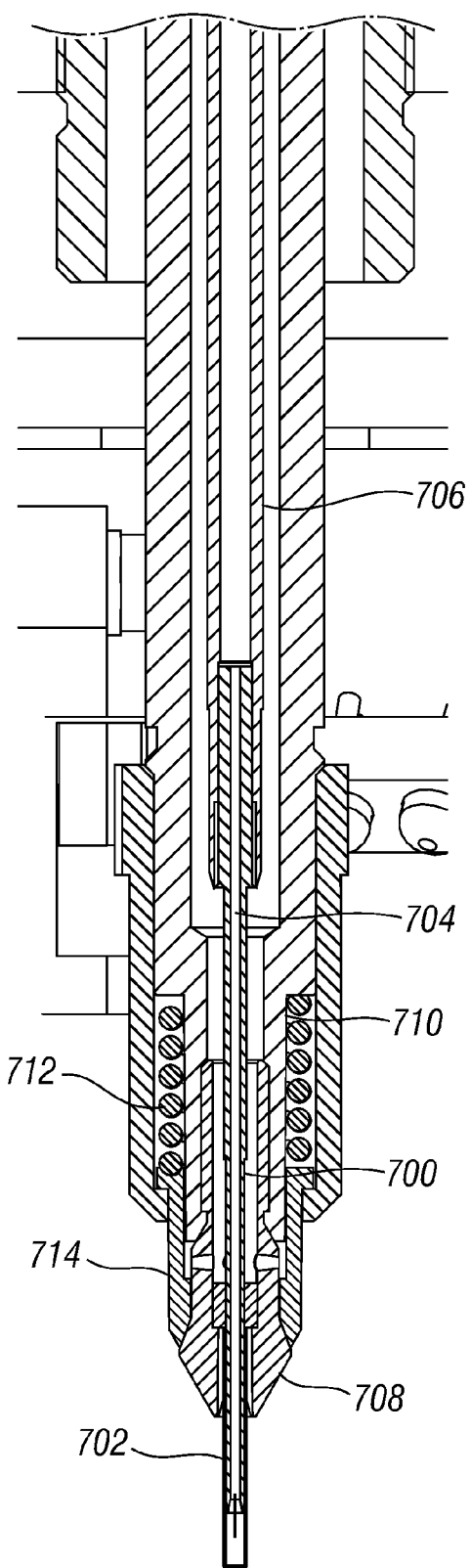
FIG. 45 is a longitudinal sectional view of one embodiment of a concentric tube biological unit removal tool incorporated into an exemplary substantially automated system.

FIG. 45 illustrates one embodiment of a concentric tube biological unit removal tool incorporated into an exemplary substantially automated system, such as robotic system. In this exemplary embodiment the removal tool assembly is carried on an automated (e.g., robotic) arm, so that movement of the removal tool relative to the body surface may be performed by movement of the robotic arm relative to the body surface, movement of the removal tool relative to the automated arm, or a combination of each.

FIG. 45 shows a concentric tube embodiment in which an inner tube 700 slides inside an outer tube 702. A source of reduced pressure communicates with a lumen 704 of the inner needle 700 to create a pressure differential therein for moving biological units through the lumen in a proximal direction. The inner needle may be held at the end of a linearly movable rod 706, while the outer needle is held in a collet 708 and may be rotated or oscillated relative to the inner tube through a spindle 710 on the end of which the collet mounts. A spring 712 acts in a distal direction on a sleeve 714 to maintain the jaws of the collet 708 closed.

In one preferred embodiment, the inner tube 700 has a distal tip that is sharp, or at least that has cutting segments thereon. Desirably, the inner tube 700 translates at a relatively high velocity of between 1-3 m/s, and penetrates the skin (i.e., body surface) to a depth of between 0.25-3.0 mm. After initially penetrating the skin, the inner tube 700 remains under the surface while the outer tube 702 follows. The outer tube 702 is desirably relatively dull compared to the inner tube 700, and enters the skin through the incision that the inner tube 700 created. The outer tube 702 stretches the skin to make the incision somewhat bigger, and enters at a slower velocity, for example, of between 1.0-25.0 mm/s. As mentioned, the outer tube 702 may be rotated or oscillated during its advance. After the outer tube 702 enters the skin, the inner tube 700 may move in concert with the outer tube, remain stationary, or retract as the outer tube continues farther into the skin. Likewise, both tubes 700, 702 may retract from the skin simultaneously, or separately, and may retract at the same or different velocities. As mentioned, suction is desirably applied within the inner tube lumen 704 to aid in biological unit retention. In addition, suction may be applied between the inner and outer tubes 700, 702, and fluids or gas may be supplied between the tubes to aid in retention.

FIGS. 46A and 46B are perspective views of yet another embodiment of the biological unit removal tool 750 incorporated in an exemplary robotically-operated system 752 for hair removal and implantation. A bank of LEDs 754 illuminates a body surface in front of the system so that an imaging device 756, such as a pair of cameras in the illustrated embodiment, obtains a clear picture for transmission back to a monitor (not shown). Various components are mounted for rotation or linear translation of the removal tool 750 at the distal end of the system. Stepper motors, hydraulic cylinders, and the like may be used, and will not be described in great detail herein.

The system may further incorporate a fluid (e.g., saline) delivery subsystem 760 as seen in FIG. 46B near the distal end of the removal tool, similar to the system described above with respect to FIGS. 37A/37B. FIG. 46B also shows an inner tube 770 having a crown-shaped distal tip 772 and a retention device therein 774. An outer tube 776 surrounds the inner tube 770. Fluid may be delivered in a concentric space between the two tubes 770, 776.

FIG. 46A also illustrates an exemplary subsystem for moving the inner and outer tubes 770, 776 together and with respect to one another. In particular, the inner tube 770 extends along an axis of the subsystem in a proximal direction and is held within a clamp 780 fixed with respect to a movable piston 782. The piston 782 reciprocates within a gas cylinder 784 depending on the pressure within the cylinder, which is controlled by a pneumatic subsystem that will be apparent to one of skill in the art. A distal end of an elongated flexible tube 786 abuts a proximal end of the inner tube 770 within a clamp 780, and defines a continuous extension of the lumen within the inner tube. As mentioned, a suction may be created within the inner tube 770, which continues through the flexible tube 786. The proximal end of the flexible tube 786 engages a storage cartridge (not shown) for receiving and holding follicular units. It should be noted that the inner tube 770 extends a significant length beyond the outer tube 776, and therefore it should be understood that the aforementioned exemplary lengths for the removal tools applies just to the outer tube 776.

The outer tube 776 also reciprocates with a piston 790 within a gas cylinder 792. In particular, a leading end nut 794 holds the outer tube 776 fixed relative to the piston 790. In the illustrated embodiment, as seen in FIG. 46B, the fluid delivery subsystem 760 is located on a distal end of the nut 794. In addition, a gear 796 is keyed to and rotates the piston 790, and thus the outer tube 776. In this particular system, therefore, the inner and outer tubes 760, 776 translate coaxially with respect to one another (or in concert) and are displaced by independently controlled piston/cylinder mechanisms. Of course, the mechanisms for linearly displacing the two tubes 760, 776 may be linear motors or other alternatives. Furthermore, the outer tube 776 rotates with respect to the inner tube 760, and may be rotated in a constant or pulsed manner as it travels in a distal direction over the inner tube 760 and into the skin, as mentioned above.

With an understanding of the aforementioned alternatives for biological unit removal tools, and in conjunction with the exemplary movement subsystem of FIG. 46A, the reader will understand the range of possible uses for the present invention. In a preferred configuration, the subsystem shown in FIG. 46A can, with the help of the visualization tools 754, 756 and a computer monitoring subsystem (not shown), rapidly remove follicular units from a body surface and transfer them to a storage device. One example of a storage device that could be incorporated into an automated system, such as robotic system, for use with the present invention, is shown and described in co-pending Application Ser. No. 60/997,188 filed Sep. 29, 2007 in reference to an exemplary system for robotic hair transplantation.

The structural parameters for the inner and outer tubes 770, 776 are desirably the same as described above for the concentric tubes 700, 702 of FIG. 45. During use, the entire subsystem 752 maneuvers into position (under the control of larger prime movers) so as to locate the distal tip 772 over a particular follicular unit to be removed. In this regard, the visualization subsystem 754, 756 is extremely valuable in pinpointing the location and orientation of the visible hair follicle. The piston/cylinder combination 782, 784 then actuates to punch the inner tube 770 into the skin to a depth of up to 3 mm and at a very high velocity (for example, 1-3 m/s). Preferably, as mentioned, the distal tip 772 includes both sharp and dull segments so that transection of the hair follicles is minimized. Subsequently, the piston/cylinder combination 790, 792 and gear 796 translates with rotation the outer tube 776 over the inner tube 770 in a distal direction. The outer tube 776 desirably has a relatively dull distal tip which enters the circular incision that the inner tube 770 created. The outer tube 776 proceeds at a relatively slow velocity of 1-25 mm/s past the end of the inner tube 770 and to a depth of approximately 5-7 mm, surrounding the targeted hair follicle. Suction may be applied to the lumen of the inner tube 770 which continues through the lumen of the outer tube 776 and helps pull free the follicular unit. Also, fluid may be applied by the subsystem 760 to the space between the two tubes to further help remove the follicular unit. Retraction of the outer tube 776, preferably in conjunction with the inner tube 770 and, also in some preferred embodiments with the help of the retention device 774, fully removes the follicular unit from the body surface.

The foregoing illustrated and described embodiments of the invention are susceptible to various modifications and alternative forms, and it should be understood that the invention generally, as well as the specific embodiments described herein, are not limited to the particular forms or methods disclosed, and that many other embodiments are possible within the spirit and the scope of the present invention. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

It will be further appreciated by those skilled in the art that the invention is not limited to the use of a particular system, and that automated (including robotic), semi-automated, and manual systems and apparatus may be used for positioning and actuating the respective removal tools and other devices and components disclosed herein. By way of another example, it will be appreciated by those skilled in the art that while some of the removal tool and apparatus embodiments are described herein in the context of harvesting tissue plugs including hair follicular units, the tools and apparatus are not limited to the harvesting of hair follicular units, and may be equally used for removing various biological units.

While the invention has been described in its preferred embodiments, it is to be understood that the words which have been used are words of description and not of limitation. Therefore, changes may be made within the appended claims without departing from the true scope of the invention.

What is claimed is:

1. A method of removing biological tissue from a donor area, comprising:
    rapidly advancing an outer elongated body to penetrate the donor area, the outer elongated body having a distal tip configured to cut through tissue;
    halting the advancement of the outer elongated body at a first depth;
    advancing an inner elongated body having a lumen sized to receive a biological unit more slowly than the rapid advancement of the outer elongated body and concentrically relative to the outer elongated body so that a distal tip of the inner elongated body extends past the first depth to a second depth, the distal tip of the inner elongated body being relatively more dull than the distal tip of the outer elongated body; and
    withdrawing the inner and outer elongated bodies to remove the biological unit from the donor area.

2. The method of claim 1, wherein the inner and the outer elongated bodies are simultaneously withdrawn, or withdrawing of the inner elongated body is initiated after or before the withdrawal of the outer elongated body is initiated.

3. The method of claim 1, wherein the method is performed manually, semi-automatically, fully automated, or comprises the use of a robotic system.

4. The method of claim 1, comprising rotating the inner elongated body, the outer elongated body, or both at least during a portion of advancement into the donor area.

5. The method of claim 1, comprising rotating the inner and/or the outer elongated body off the axis relative to the other to cause the respective elongated body to wobble.

6. The method of claim 1, comprising supplying a fluid or gas under pressure to the distal tip of one or both of the outer and inner elongated bodies.

7. The method of claim 6, comprising actuating a fluid dispensing subsystem using one or more computer-controlled mechanisms.

8. The method of claim 1, wherein the biological unit is a follicular unit and wherein the method further comprises harvesting the follicular unit from a body surface.

9. The method of claim 1, comprising removing the biological unit from the donor area for transplantation into a recipient area.

10. The method of claim 1, comprising monitoring operation of the inner and/or outer elongated body with a use of a visualization subsystem and transmitting the monitored information to a display.

11. The method of claim 1, comprising applying suction within the lumen of the inner elongated body.

12. The method of claim 1, wherein the inner elongated body comprises a retention member configured to retain the biological unit received in the lumen of the inner elongated body, the method further comprising activating the retention member to achieve a retention position to impede movement of the biological unit in the distal tip direction.

13. The method of claim 12, wherein the activating the retention member is automatically controlled by a robotic system or comprises activating via an electronically controlled actuation mechanism.

14. The method of claim 12, wherein the retention member comprises a plurality of retention members, a tapered insert, at least one continuous rib around an internal circumference of the elongated body, a spring, an accordion-like structure, a balloon, grooves, a plurality of discrete circumferentially-spaced retention members, a bendable finger, one or more windows, slots or one or more movable retention members.

15. The method of claim 12, wherein the retention member is formed of a deformable material or atraumatic material, or shaped with non-traumatic edges.

16. The method of claim 1, wherein the distal tip of the inner and/or outer elongated body comprises a series of alternating cutting and relief segments and wherein the cutting segments and the relief segments alternative in a repeating pattern with constant spacing or with variable spacing.

17. The method of claim 16, wherein at least some of the relief segments define a smooth curve between the two adjacent cutting segments.

18. The method of claim 1, wherein the inner elongated body comprises a spring member configured to normally bias the outer elongated body distally relative to the inner elongated body, and the method further comprises causing the outer elongated body to move in a proximal direction relative to the inner elongated body as the outer elongated body is pressed against a skin of the donor area.

19. The method of claim 18, wherein the outer elongated body comprises a slot and the inner elongated body comprises a pin, the method further comprises moving the pin axially within the slot.

20. The method of claim 1, wherein the distal tip of the inner elongated body, the outer elongated body, or both has an internal or external taper.

* * * * *